US010993732B2

(12) United States Patent
Bashir et al.

(10) Patent No.: US 10,993,732 B2
(45) Date of Patent: *May 4, 2021

(54) INFUSION CATHETER AND METHOD OF USE

(71) Applicant: Temple University-Of The Commonwealth System of Higher Education, Philadelphia, PA (US)

(72) Inventors: Riyaz Bashir, Mount Laurel, NJ (US); Nicholas A. Green, Jupiter, FL (US)

(73) Assignees: Temple University—Of The Commonwealth System of Higher Education, Philadelphia, PA (US); THROMBOLEX, INC., New Britain, PA (US)

( * ) Notice: Subject to any disclaimer, the term of this patent is extended or adjusted under 35 U.S.C. 154(b) by 112 days.

This patent is subject to a terminal disclaimer.

(21) Appl. No.: 16/131,390

(22) Filed: Sep. 14, 2018

(65) Prior Publication Data

US 2019/0021751 A1 Jan. 24, 2019

Related U.S. Application Data

(63) Continuation of application No. 15/799,030, filed on Oct. 31, 2017, now Pat. No. 10,123,814, which is a
(Continued)

(51) Int. Cl.
*A61M 25/00* (2006.01)
*A61B 17/221* (2006.01)
(Continued)

(52) U.S. Cl.
CPC ............ *A61B 17/221* (2013.01); *A61B 17/22* (2013.01); *A61B 18/00* (2013.01); *A61M 25/007* (2013.01); *A61M 25/0043* (2013.01); *A61M 25/0108* (2013.01); *A61B 17/320725* (2013.01); *A61B 2017/00871* (2013.01); *A61B 2017/2217* (2013.01); *A61B 2017/22038* (2013.01); *A61B 2017/22084* (2013.01);
(Continued)

(58) Field of Classification Search
CPC .... A61M 2025/0057; A61M 2025/105; A61M 25/007; A61B 17/221; A61B 17/22; A61B 17/320725
See application file for complete search history.

(56) References Cited

U.S. PATENT DOCUMENTS 5,250,034 A 10/1993 Appling
5,456,676 A 10/1995 Nelson
(Continued)

*Primary Examiner* — Laura A Bouchelle
(74) *Attorney, Agent, or Firm* — Riverside Law LLP

(57) ABSTRACT

An infusion catheter has an elongate flexible shaft including a wall and a lumen extending between a proximal end and a distal end. The catheter also has a sealing member within the shaft lumen including a wall and a lumen. The catheter also has a slidable, retractable elongate central axis member extending through the shaft and sealing member lumens connected to an end cap. The catheter also has a plurality of eluting arms extending radially around the central axis member, including lumens fluidly connected to the shaft lumen and the distal end cap. A method for treating a thrombus is also disclosed.

25 Claims, 20 Drawing Sheets

Related U.S. Application Data continuation of application No. PCT/US2017/027828, filed on Apr. 15, 2017.

(60) Provisional application No. 62/322,881, filed on Apr. 15, 2016, provisional application No. 62/414,328, filed on Oct. 28, 2016.

(51) Int. Cl.
*A61B 17/22* (2006.01)
*A61B 18/00* (2006.01)
*A61M 25/01* (2006.01)
*A61B 17/3207* (2006.01)
*A61B 17/00* (2006.01)

(52) U.S. Cl.
CPC . *A61M 25/0074* (2013.01); *A61M 2025/0057* (2013.01); *A61M 2205/0266* (2013.01)

(56) References Cited

U.S. PATENT DOCUMENTS

| | | |
|---|---|---|
| 5,591,137 A | 1/1997 | Stevens |
| 5,599,328 A | 2/1997 | Stevens |
| 5,616,203 A | 4/1997 | Stevens |
| 5,651,170 A | 7/1997 | Stevens |
| 5,957,865 A | 9/1999 | Backman |
| 5,957,901 A | 9/1999 | Mottola |
| 6,179,816 B1 | 1/2001 | Mottola |
| 6,280,413 B1 | 8/2001 | Clark |
| 6,623,452 B2 * | 9/2003 | Chien ............... A61M 25/10 604/101.01 |
| 6,663,613 B1 | 12/2003 | Evans |
| 6,852,097 B1 | 2/2005 | Fulton, III |
| 6,955,661 B1 * | 10/2005 | Herweck ............. A61L 29/041 604/264 |
| 8,187,222 B2 * | 5/2012 | Weber ............... A61M 31/002 604/103.02 |
| 8,774,913 B2 | 7/2014 | Demarais |
| 10,123,814 B2 * | 11/2018 | Bashir ............. A61M 25/0043 |
| 2001/0031981 A1 | 10/2001 | Evans |
| 2010/0016832 A1 | 1/2010 | Thai |
| 2010/0069838 A1 | 3/2010 | Weber |
| 2010/0168647 A1 | 7/2010 | Tegg |
| 2011/0276022 A1 | 11/2011 | O'Day |
| 2013/0282084 A1 | 10/2013 | Mathur |
| 2014/0039484 A1 | 2/2014 | Leung |

* cited by examiner

INFUSION CATHETER AND METHOD OF USE

CROSS-REFERENCE TO RELATED APPLICATIONS

This application is continuation of U.S. patent application Ser. No. 15/799,030, filed Oct. 31, 2017, which is a continuation of International Application No. PCT/US17/27828, filed Apr. 15, 2017, which claims priority to U.S. Provisional Patent Application No. 62/322,881 filed Apr. 15, 2016; and U.S. Provisional Patent Application No. 62/414,328 filed Oct. 28, 2016, the contents of which are each incorporated by reference herein in their entireties.

BACKGROUND OF THE INVENTION

Venous thromboembolic disease (VTE) is estimated to occur in more than 1.4 to 2.2 per 1000 persons annually, manifesting as deep vein thrombosis (DVT) and/or pulmonary embolism (PE). It is the cause of over 180,000 deaths annually, more than motor vehicle accidents, breast cancer, and AIDS combined, and is the most preventable cause of death in hospitalized patients in the United States. Despite treatment with anticoagulant therapy, a significant proportion of survivors of acute VTE are likely to suffer from the disabling sequelae, such as post thrombotic syndrome (PTS), recurrent VTE, or chronic thromboembolic pulmonary hypertension (CTEPH).

PTS occurs in 20-50% of patients with proximal lower extremity VTE. PTS is characterized by lower extremity chronic pain, swelling, feeling of heaviness, fatigue, pruritus, hyperpigmentation, and skin ulcerations. PTS causes a lifelong physical, social, and psychological disability and markedly impairs quality of life, worse than that of other chronic diseases like osteoarthritis, angina pectoris, and chronic lung disease. PTS and chronic venous disease create a considerable economic burden on society and lead to more than 200 million workdays lost each year in US.

Up to 16% of patients with acute pulmonary embolism go on to develop CTEPH, which leads to a very debilitating shortness of breath and right heart failure. This condition markedly impairs quality of life and the only effective and durable treatment is restricted to a major open-heart surgery called pulmonary thromboembolectomy (PTE). This surgery and its post-operative management are so complex that only a handful of centers around the globe offer this to their patients. Given the limitations of current medical therapy, promising endovascular treatment modalities have evolved over the past 2 decades in an effort to mitigate the acute and chronic disability from VTE. In fact, data from the US suggests rapid adoption of these catheter-based thrombus removal techniques is already underway.

Unfortunately the current state of technology is limited to using those endovascular devices that were originally developed for small vessels in the affected large vessels such as pulmonary arteries or inferior vena cava. This has led to suboptimal thrombus removal in current clinical practice. It was this clinical experience that became the inspiration to develop devices dedicated for large vessels.

Conventional methods for catheter-directed thrombolysis involves infusing a clot dissolving medication via a single lumen infusion catheter, which typically measures at a maximum 1.5 mm in diameter. The catheter is placed in a vessel which is 10 to 15 times larger than the catheter and is completely full of blood clot with no blood flow through the vessel or into the clot. Since there is no flow through the vessel, the clot dissolving medication often never reaches the clot, and it becomes necessary to advance the catheter inside the clot and direct a low dose of the thrombolytic medication directly into the clot. However, this technique is limited to dissolving the clot along a singular pathway and performance is relatively poor for dissolving large volume clots in large vessels.

EkoSonic Endovascular Systems (Ekos Corporation), a BTG International group company, uses a combination of standard single lumen catheterization techniques to deliver thrombolytics directly into the thrombus and ultrasound energy to loosen the fibrin strands within the clot to accelerate the thrombolytic process. Other single lumen infusion catheters on the market include the Fountain catheter (Merit Medical systems Inc. South Jordan Utah), Unifuse catheter (Angiodynamics, Latham, N.Y.), and Craig McNamara catheter (Medtronic, Minneapolis Minn.). Other competitive products on the market or in development include those devices used for mechanical thrombectomy, such as AngioJet (Boston Scientific, Marlborough Mass.), Penumbra (Penumbra, Alameda, Calif.), AngioVac, veno-venous bypass with filtration (Angiodynamics Latham N.Y.), Inari Flow Retriever (Inari Medical Irvine, Calif.), and MegaVac (Capture Vascular Inc. Mountain village, Colo.).

Currently, none of the devices that are available on the market or in development are capable of mechanically opening up a passage within the thrombus to harness the body's own indigenous clot dissolving substances (endogenous fibrinolysis) without fragmentation of the thrombus, which may lead to embolization of the fragments into vessels that are normally functioning at baseline. For example, the Ekos Catheter was originally designed for use in smaller peripheral vasculature, not in large vessels like the inferior vena cava or pulmonary arteries. This limitation is much more profound in currently available single lumen infusion catheters. The AngioJet System has a 15 year history, and has a black box warning by the FDA for pulmonary embolism. The AngioVac device requires a patient to be on a veno-venous bypass pump, which requires an operating room and perfusionists. It is technically very difficult to get to the pulmonary artery and requires personnel from multiple specialties to operate, and as a result, this technology is not readily available in most hospital environments. Fragmentation of the thrombus can lead to embolization into normally functioning segments of the lung, which can make patients very sick. Surgical embolectomy is rarely used in these patients (0.6% of all pulmonary embolism cases).

What is needed in the art is an improved infusion catheter that is more effective at dissolving large volume clots in large vessels. The present invention meets this need.

SUMMARY OF THE INVENTION

In one embodiment, an infusion catheter comprises an elongate flexible shaft comprising a wall and a lumen extending a length between a proximal end and a distal end; a sealing member within the shaft lumen comprising a wall and a lumen extending a length between a proximal end and a distal end, the distal end of the sealing member being attached to the distal end of the shaft; a slidable, retractable elongate central axis member extending through the shaft and sealing member lumens and connecting to a distal end cap; and a plurality of eluting arms, each eluting arm having a lumen fluidly connected to the distal end of the shaft lumen, extending radially around the central axis member, and connecting to the distal end cap. In one embodiment, the infusion catheter further comprises a frame having a plurality of tines, each tine within the lumen of each eluting arm. In one embodiment, the frame is constructed from a shape memory material. In one embodiment, the shape memory material is nitinol. In one embodiment, the shape memory material forms a spiral shape. In one embodiment, the shape memory material forms a pear shape. In one embodiment, each eluting arm comprises a plurality of infusion ports fluidly connected to the lumen of each eluting arm. In one embodiment, the infusion ports are laser drilled holes having diameters between 0.001 and 0.01 inches. In one embodiment, each eluting arm comprises a porous surface. In one embodiment, the porous surface elutes pressurized fluid from each eluting arm lumen. In one embodiment, the porous surface is constructed from a material selected from the group consisting of: polytetrafluoroethylene (PTFE), expanded PTFE (ePTFE), Tyvek, and Kynar polyvinylidene fluoride (PVDF). In one embodiment, each eluting arm is positioned within an outer tube having a surface comprising a plurality of infusion ports fluidly connected to a lumen, a closed proximal end, and a closed distal end. In one embodiment, the surface of each outer tube is less porous than each eluting arm. In one embodiment, the inner diameter of the sealing member lumen and the outer diameter of the central axis member are dimensioned such that central axis member slip fits within the sealing member lumen with a close clearance permitting movement in the central axis member while preventing fluid leakage through the close clearance. In one embodiment, the central axis member is slidable through the sealing member lumen and the shaft lumen, the shaft lumen having a fluid pressure higher than a fluid pressure outside of the shaft lumen, without leaking fluid through the close clearance. In one embodiment, the distance between the distal end cap and the distal end of the shaft is reversibly shortened by sliding central axis member through the sealing member lumen, thereby expanding the plurality of eluting arms away from the central axis member. In one embodiment, the central axis member comprises a guidewire lumen.

A method for treating thrombus in a vessel includes advancing a catheter at least partially through a thrombus within a vessel, the catheter having a sealing lumen positioned at a distal end, a slidable elongate central axis member running through the catheter and the sealing lumen and connected to a distal end cap, and a plurality of eluting arms extending radially around the central axis member connecting the distal end of the catheter with the distal end cap; expanding the plurality of eluting arms of the catheter within the thrombus and away from the central axis member; and infusing a therapeutic agent through a plurality of infusion ports in the plurality of eluting arms. In one embodiment, the step of expanding comprises retracting the central axis member such that the distance between the distal end of the catheter and the distal end cap is shortened. In one embodiment, the plurality of eluting arms is expanded to a spiral shape. In one embodiment, the plurality of eluting arms is expanded to a pear shape.

In one embodiment, an infusion catheter includes an elongate flexible shaft comprising a wall, a lumen and a longitudinal axis extending between a proximal end and a distal end; wherein the wall comprises a first plurality of infusion ports facing towards the longitudinal axis and a second plurality of infusion ports facing away from the longitudinal axis; and wherein a portion of the elongate flexible shaft comprises a shape memory material configured to move the wall away from the longitudinal axis in a relaxed state. In one embodiment, the wall along the portion of the elongate flexible shaft comprises the shape memory material. In one embodiment, the shape memory material is a shape memory polymer. In one embodiment, a shape memory component positioned within the lumen along the portion of the elongate flexible shaft comprises the shape memory material. In one embodiment, the shape memory material is a medical grade metal. In one embodiment, the shape memory material is nitinol. In one embodiment, the portion of the elongate flexible shaft comprising the shape memory material forms a spiral shape in the relaxed state. In one embodiment, the portion of the elongate flexible shaft comprising the shape memory material forms a conical spiral shape in the relaxed state. In one embodiment, the conical spiral shape tapers distally towards the longitudinal axis. In one embodiment, the portion of the elongate flexible shaft comprising the shape memory material further comprises a plurality of branches that diverge away from the longitudinal axis distally from a first point along the longitudinal axis and converge towards the longitudinal axis distally to a second point along the longitudinal axis in the relaxed state. In one embodiment, the branches comprise a plurality of branch lumens that are all in fluid communication with the lumen. In one embodiment, the branches comprise the first and second plurality of infusion ports. In one embodiment, one of the first point and second point is fixed to a central wire, while the other of the first point and second point is coaxially loaded and slidable over the central wire. In one embodiment, a proximal radiopaque marker is included on an outer surface of the wall proximal of the portion of the elongate flexible shaft comprising the shape memory material; and a distal radiopaque marker on an outer surface of the wall distal of the portion of the elongate flexible shaft comprising the shape memory material. In one embodiment, the portion of the elongate flexible shaft comprising the shape memory material is between 9 and 11 centimeters long in the relaxed state. In one embodiment, the portion of the elongate flexible shaft comprising the shape memory material is between 3 and 30 centimeters long in the relaxed state. In one embodiment, the wall moves between 2 and 10 millimeters away from the longitudinal axis in the relaxed state. In one embodiment, the wall moves substantially 5 millimeters away from the longitudinal axis in the relaxed state. In one embodiment, the lumen terminates at the distal end in a guidewire opening. In one embodiment, an infusion system kit includes: the infusion catheter of the present invention; and a guidewire configured for insertion through a guidewire lumen of the central axis member.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which.

DETAILED DESCRIPTION OF THE INVENTION

Figure 1A:
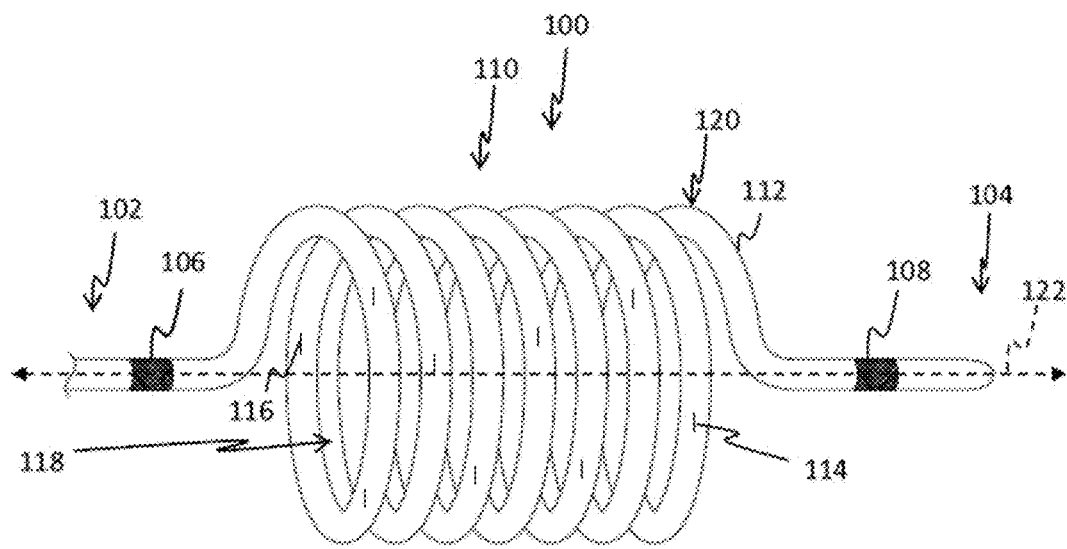
FIG. 1A and FIG. 1B show an infusion catheter with spiral shape memory according to one embodiment.

It is to be understood that the figures and descriptions of the present invention have been simplified to illustrate elements that are relevant for a more clear comprehension of the present invention, while eliminating, for the purpose of clarity, many other elements found in systems and methods of treating pulmonary embolism and deep vein thrombosis. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Ranges: throughout this disclosure, various aspects of the invention can be presented in a range format. It should be understood that the description in range format is merely for convenience and brevity and should not be construed as an inflexible limitation on the scope of the invention. Where appropriate, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Referring now in detail to the drawings, in which like reference numerals indicate like parts or elements throughout the several views, in various embodiments, presented herein is an infusion catheter and a method for treating pulmonary embolism and deep vein thrombosis.

Figure 1B:
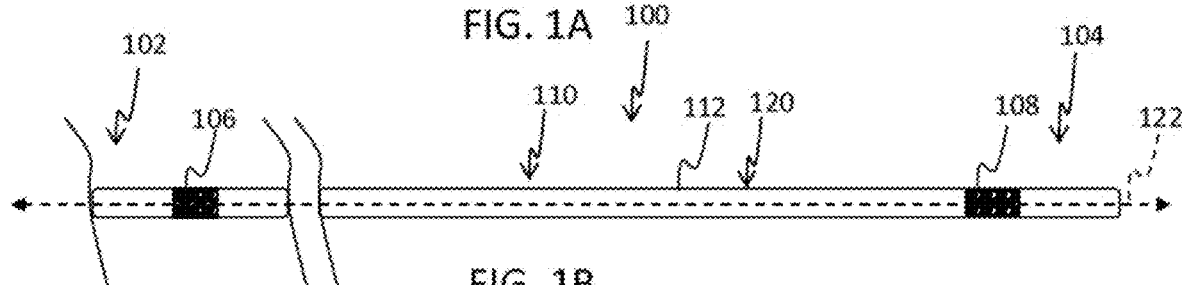

With reference now to the embodiment in FIG. 1A and FIG. 1B, an infusion catheter 100 has an elongate flexible shaft 120 including a wall 112 that forms an internal lumen extending through the elongate flexible shaft 120. A longitudinal axis 122 extends between a proximal end 102 and a distal end 104 of the shaft 120 through the center of the lumen when the catheter 100 is in a straightened position (e.g. FIG. 1B). When the shaft 120 is in a relaxed state (e.g. FIG. 1A), the catheter 100 reverts to a predetermined shape formed by shape memory materials. In one embodiment, a portion 110 of the catheter 100 includes a shape memory polymer within the polymer wall 112 material for forming the desired shape. In another embodiment, a shape memory metal such as nitinol is inserted within the lumen of the polymer wall for forming the desired shape. In another embodiment, the shape memory metal in molded into the bulk of the catheter wall, or attached to the outside of the catheter wall.

Figure 1C:
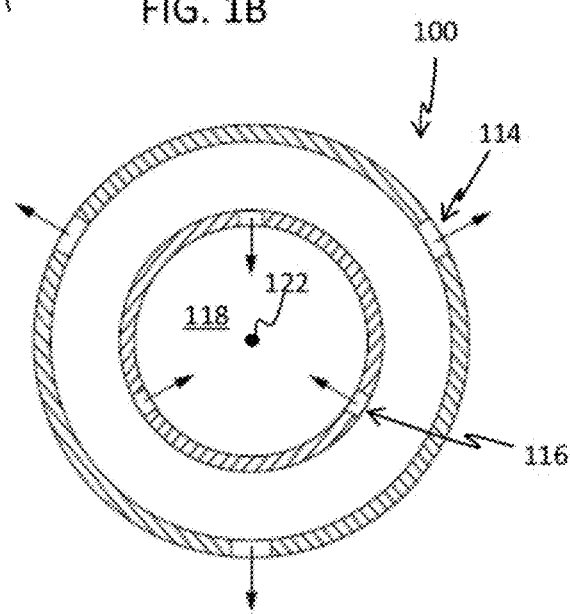
FIG. 1C is an exemplary diagram of the directions of fluid infusion.

In the relaxed state, the shaft 120 forms an interior core 118 radially disposed about the longitudinal axis 122. Illustrated in FIG. 1C, when the elongate flexible shaft 120 is in the relaxed state, the wall 112 has a first set of infusion ports 116 facing towards the longitudinal axis 122 and interior core 118, and a second set of infusion ports 114 facing away from the longitudinal axis 122. In certain embodiments, the infusion ports are openings that are always at least partially open. In certain embodiments, the infusion ports pressure are pressure actuated ports such as slits. In certain embodiments that utilize slits, the slits are configured to open only when a threshold fluid pressure is attained within the lumen. Other infusion ports known in the art can also be utilized. When the elongate flexible shaft 120 transitions from a straightened or stressed state into the relaxed state, the shape memory material moves the walls 112 of the catheter 100 within portion of the catheter 100 having the shape memory material away from the longitudinal axis 122. Advantageously, the catheter allows for mechanical movement of the catheter to exert pressure on the clot for creating a large channel in the middle of the clot, therefore enhancing blood flow through the clot. The increased flow of blood in the middle of the clot enhances the ability for the body's own clot dissolving chemicals into the clot, markedly enhancing the therapeutic effect of the clot dissolving medication. Further, the inward and outward facing infusion ports throughout the 3-dimensional bulk of the clot provides a superior pattern for delivering clot dissolving medication. This improved infusion port distribution throughout the clot combined with the mechanical creation of blood flow pathways through the clot for facilitating clot using the body's natural chemicals provides a synergistic effect for improved treatment of clots.

Figure 2A:
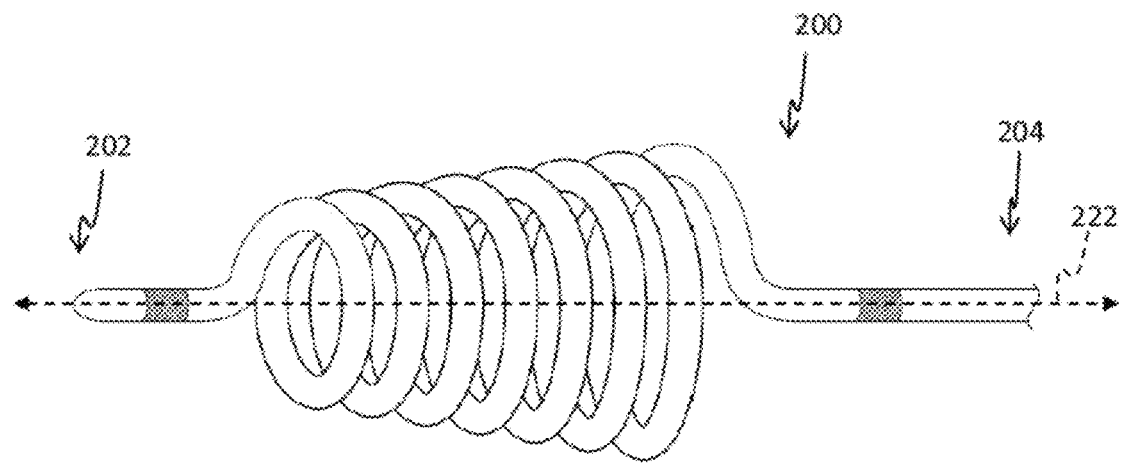
FIG. 2A shows an infusion catheter with tapered spiral shape memory according to one embodiment.
Figure 2B:
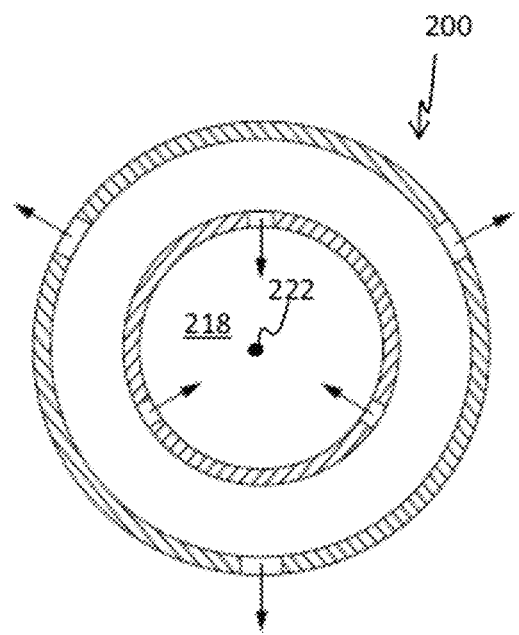
FIG. 2B is an exemplary diagram of the directions of fluid infusion.

Various shapes can be formed by the shape memory material. In one embodiment, as shown in FIG. 1A and FIG. 1B, the elongate flexible shaft comprising the shape memory material forms a spiral shape in the relaxed state. In another embodiment, as illustrated in FIG. 2A and FIG. 2B, the shape memory material of the infusion catheter 200 forms a conical spiral shape in the relaxed state. The infusion catheter 200 has a proximal end 204 and a distal end 202, and similar features described in the first embodiment are present, such as the inward and outward facing infusion ports. In certain embodiments, the conical spiral shape tapers distally towards the longitudinal axis 222, and the conical shape of the catheter wall forms a conical shaped interior core 218. Advantageously, the conical shaped core that tapers down distally facilitates the trapping and lysing of clot fragments from moving further distally through the vessel and prevents the fragments from being carried downstream through the blood, minimizing the chance for a potential embolism. Another advantage of this design is that the tighter turns at the distal tip of the catheter have a lower profile, which can facilitate easier insertion of the catheter through the clot. These embodiments can also feature infusion ports that face both towards and away from the longitudinal axis for 3-dimensional lysing.

Figure 3A:
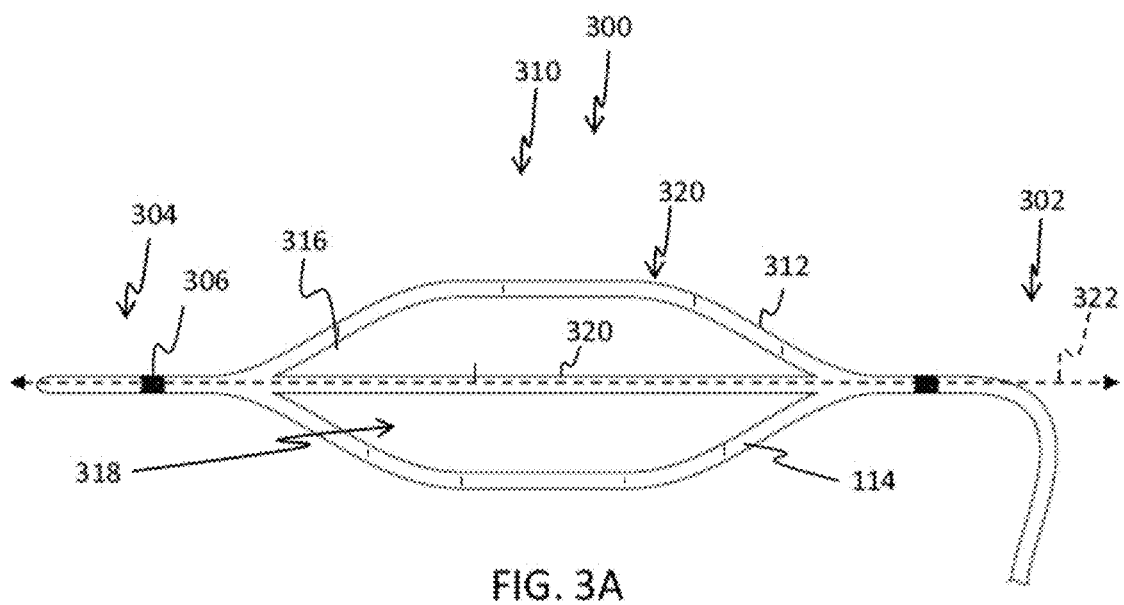
FIG. 3A and FIG. 3B show an infusion catheter with expanding branched arms according to one embodiment.
Figure 3B:
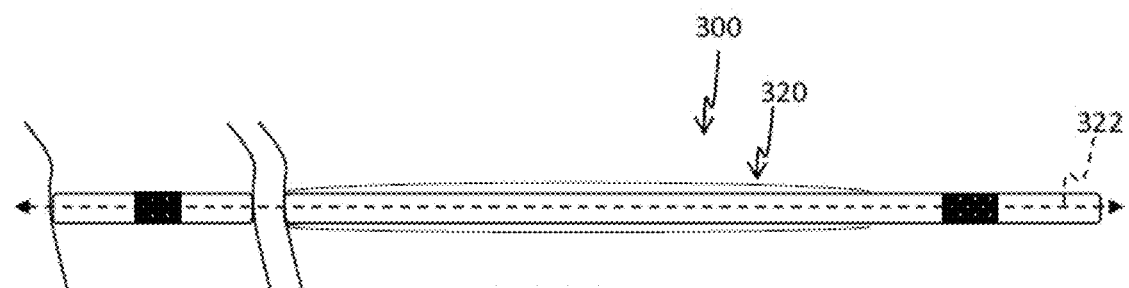

With reference now to the embodiment in FIG. 3A and FIG. 3B, an infusion catheter 300 has multiple branching arms running along a portion 310 of the catheter 300. A longitudinal axis 322 extends between a proximal end 302 and a distal end 304 of the catheter 300, through the center of the lumen in the center arm 321 when the catheter 300 is in a straightened position. When the catheter 300 is in the straightened state (e.g. FIG. 3B), the arms collapse such that the catheter has a low and generally circular profile, providing for easy insertion into a sheath and/or vessel. When the catheter 300 is in a relaxed state (e.g. FIG. 3A), the catheter 300 reverts to a predetermined shape of branches expanded away from the longitudinal axis 322 due to the use of shape memory materials. Similar to previous embodiments, the catheter 300 in this embodiment can include a shape memory polymer within the polymer wall 312 material for forming the desired shape, a shape memory metal such as nitinol is inserted within the lumen of the polymer wall for forming the desired shape, or the shape memory metal molded into the bulk of the catheter wall, or attached to the outside of the catheter wall.

Figure 3C:
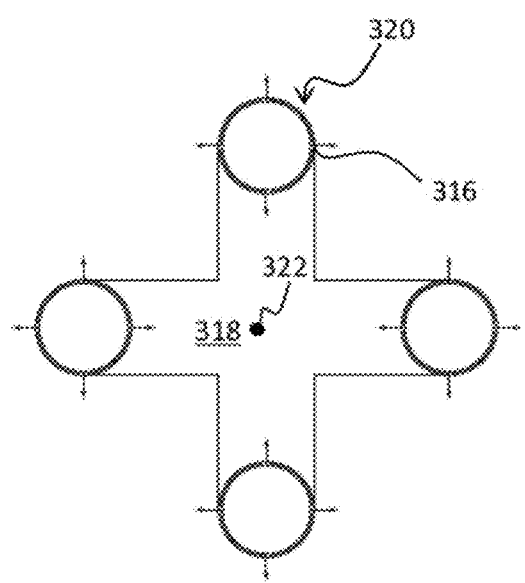
FIG. 3C is an exemplary diagram of the directions of fluid infusion.

In the relaxed state, the branching arms 320 form an interior core 318 radially disposed about the longitudinal axis 322. Illustrated in FIG. 3C, when the branching arms 320 are in the relaxed state, infusion ports 316 are facing both towards the longitudinal axis 322 and interior core 318 and away from the longitudinal axis 322. In certain embodiments, the infusion ports are openings that are always at least partially open, or they are alternatively pressure actuated ports such as slits. The lumens of the branching arms 320 can be in fluid communication with the lumens of the catheter that extend beyond the arms, to proximal and distal tips of the catheter 300.

Figure 4A:
FIG. 4A through FIG. 4C show an infusion catheter loaded over a guidewire according to one embodiment.
Figure 4B:
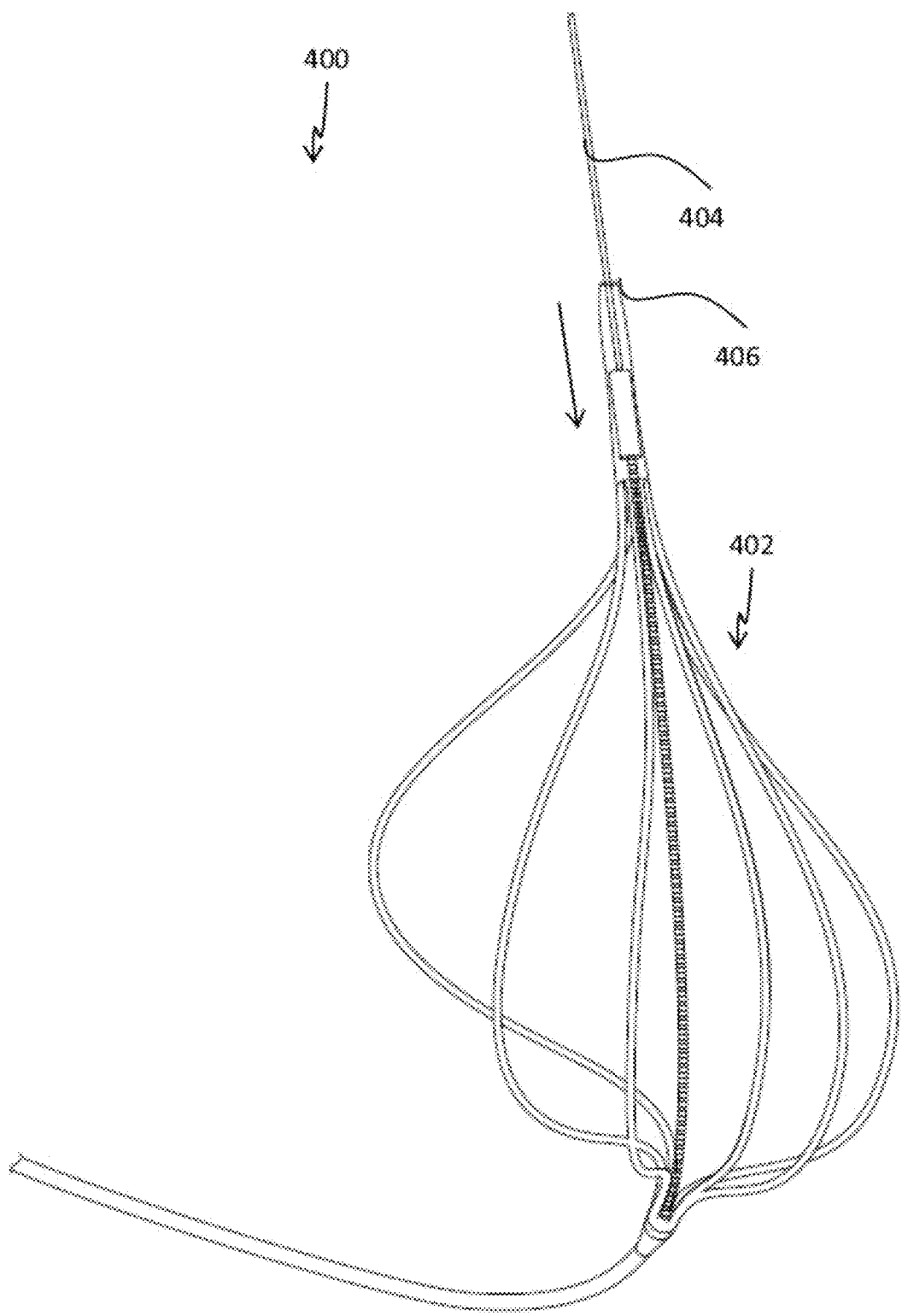
Figure 4C:
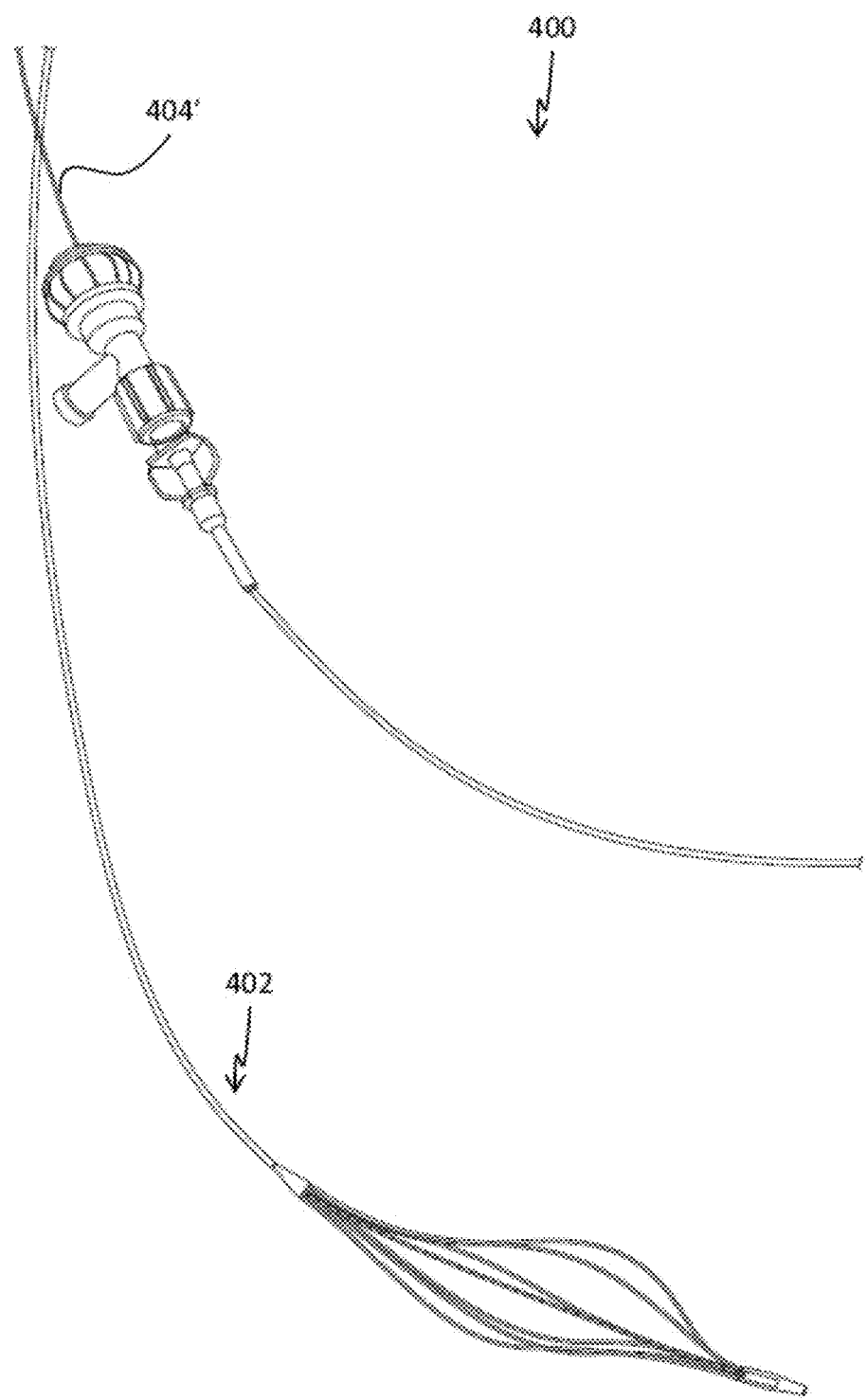

With reference now to the embodiment in FIG. 4A through FIG. 4C, an embodiment of an infusion catheter system 400 including the infusion catheter 402 loaded over a guidewire 404. The catheter and guidewire can come in a kit, and the catheter can be optionally preloaded over the guidewire. The catheter 402 can utilize shape memory components in the branching arms, for example as described in embodiments above. Embodiments shown in FIG. 4A through FIG. 4C may function with a push/pull mechanism for expanding and narrowing the arms. In one embodiment (illustrated specifically in FIG. 4B), the distal tip 406 of the catheter 402 is attached and fixed to the guidewire 404 so that as the proximal end 404' of the guidewire 404 is pulled back proximally relative to keeping the catheter 402 at the target site, the branching arms on the catheter 402 expand outwardly. In certain embodiments, the guidewire does not expand past the distal tip of the catheter 402, as shown in FIG. 4C.

Figure 5:
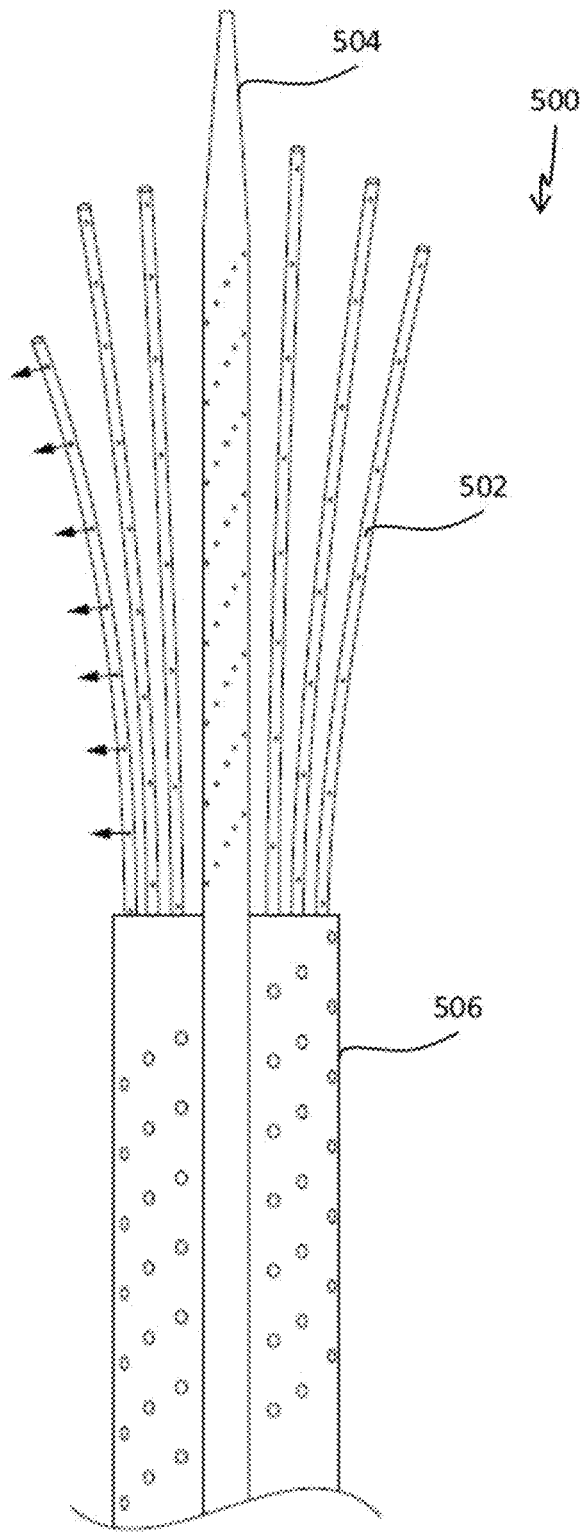
FIG. 5 is a side view of an infusion catheter having diverging tines according to one embodiment.

In the embodiment of an infusion catheter 500 shown in FIG. 5, multiple infusion tines 502 can extend from the end of the catheter 500 and continue straight or diverge away from the longitudinal axis of the catheter. Each tine can include one or more infusion ports. The tines can be uniform or varied diameters and profile shapes, such as for example having a thicker pointed tine 504 in the center for penetrating the center of a clot. Proximal portions 506 of the catheter 500 can include a catheter wall having a number of infusion ports. Infusion ports of the various embodiments described herein can be uniform or varied sizes. The infusion ports can also have varied pattern densities, such as for example greater port density (i.e. more ports or larger ports) near the center, to that lytic agents are concentrated towards the center or another particular area of the clot.

Figure 6:
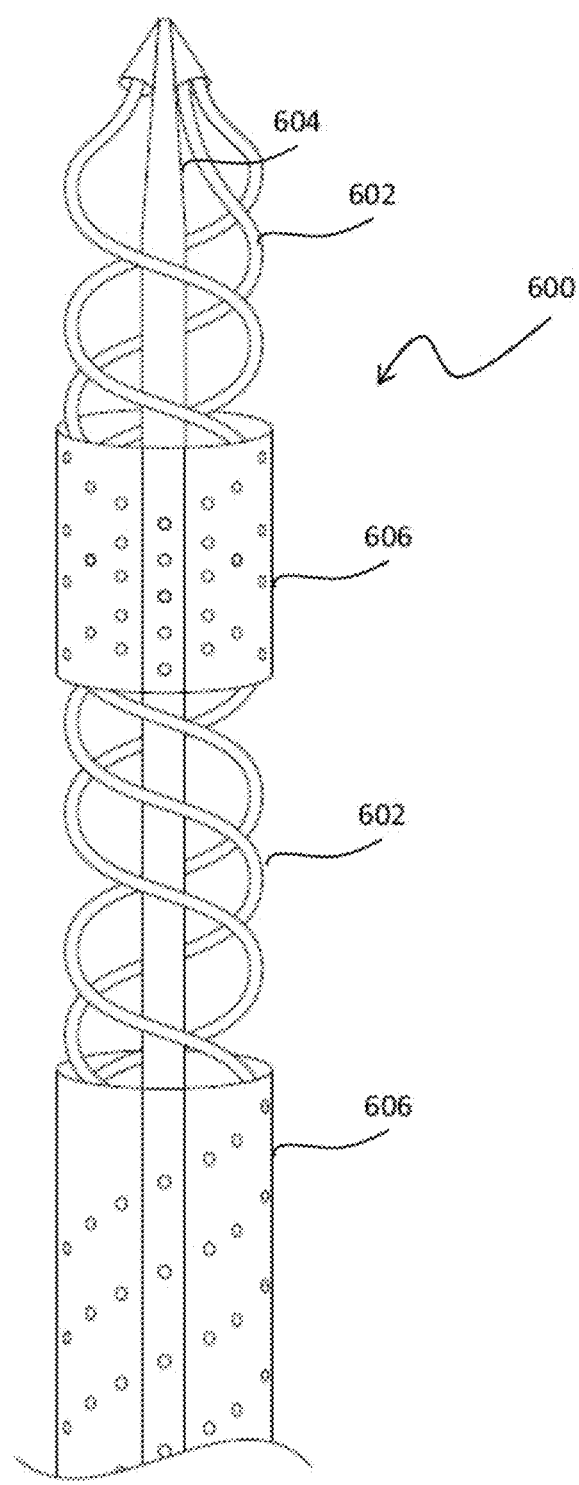
FIG. 6 is a side view of an infusion catheter with spiraled members and wall members according to one embodiment.

The embodiment of an infusion catheter 600 shown in FIG. 6 has multiple spiraled arms 602 surrounding a central conduit 604. Walled portions 606 of the catheter 600 have a call with multiple infusion ports. The spiraled arms 602 and central conduit 604 can also have multiple infusion ports. In certain embodiments, the spiraled arms 602, central conduit 604 and walled portions 606 all have lumens that are in fluid communication with each other and a lytic agent. In one embodiment, the wall 606 is expandable and it entirely encapsulated the expandable spiraled arms 606. Thus, the catheter can easily and smoothly be inserted through a clot, while also having the ability to expand through the bulk of the clot as needed.

Figure 7:
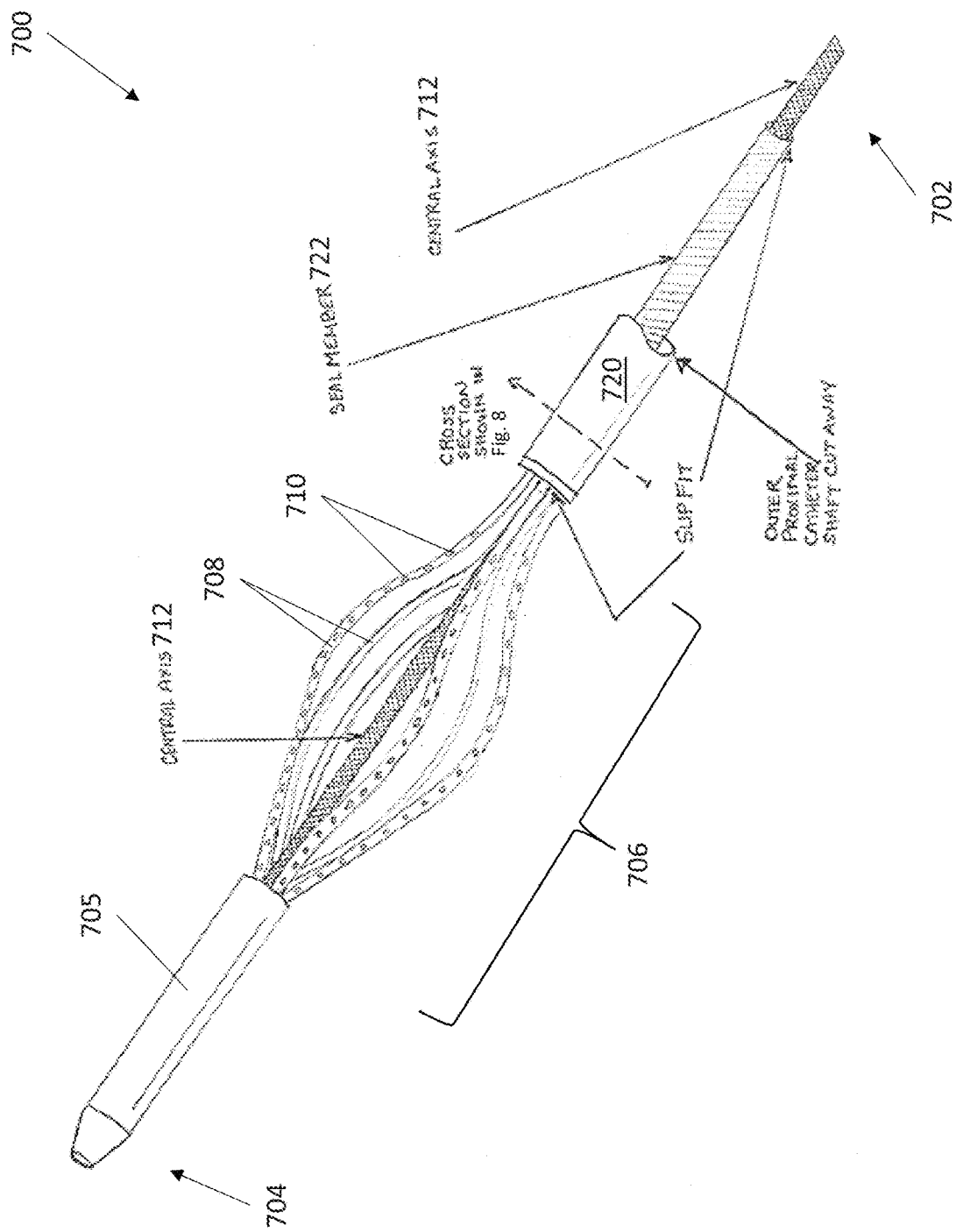
FIG. 7 is a side view of an infusion catheter with a cutaway view exposing a sealing member over a central axis member according to one embodiment.

The embodiment of an infusion catheter 700 shown in FIG. 7 has an elongate flexible shaft 720 at a proximal end 702 and an eluting portion 706 at a distal end 704 positioned between distal end cap 705 and shaft 720. Shaft 720 has a lumen running throughout. Central axis member 712 extends through shaft 720 of infusion catheter 700 from proximal end 702, exits shaft 720 to extend through eluting portion 706, and is attached to distal end cap 705 at distal end 704. The eluting portion 706 can be between 10 and 40 cm in length and has multiple flexible eluting arms 708 disposed radially around central axis member 712, with each eluting arm 708 having a lumen fluidly connected to the lumen of shaft 720. In a relaxed state, the multiple eluting arms 708 lay flat against central axis member 712, such that eluting portion 706 has substantially the same outer diameter as distal end cap 705 and shaft 720. In a stressed or deployed state, the multiple eluting arms 708 bow outwards away from central axis member 712. In various embodiments, the deployed multiple eluting arms 708 comprise a flexibility to conform to the inner geometry of a blood vessel without damaging the blood vessel. Infusion catheter 700 can be reversibly configured from a relaxed state to a stressed or deployed state by sliding central axis member 712. For example, pulling on central axis member 712 pulls distal end cap 705 closer to shaft 720, causing the multiple eluting arms 708 to bow outwards. Releasing or pushing central axis member 712 moves distal end cap 705 away from shaft 720, straightening the multiple eluting arms 708 and causing the multiple eluting arms 708 to lay flat against central axis member 712. In some embodiments, central axis member 712 is a rigid or semi-rigid shaft. In other embodiments, central axis member 712 is open at both ends and comprises a lumen running throughout, permitting the insertion of any suitable instrument, such as a guidewire, pressure sensor, temperature sensor, and the like.

Figure 8:
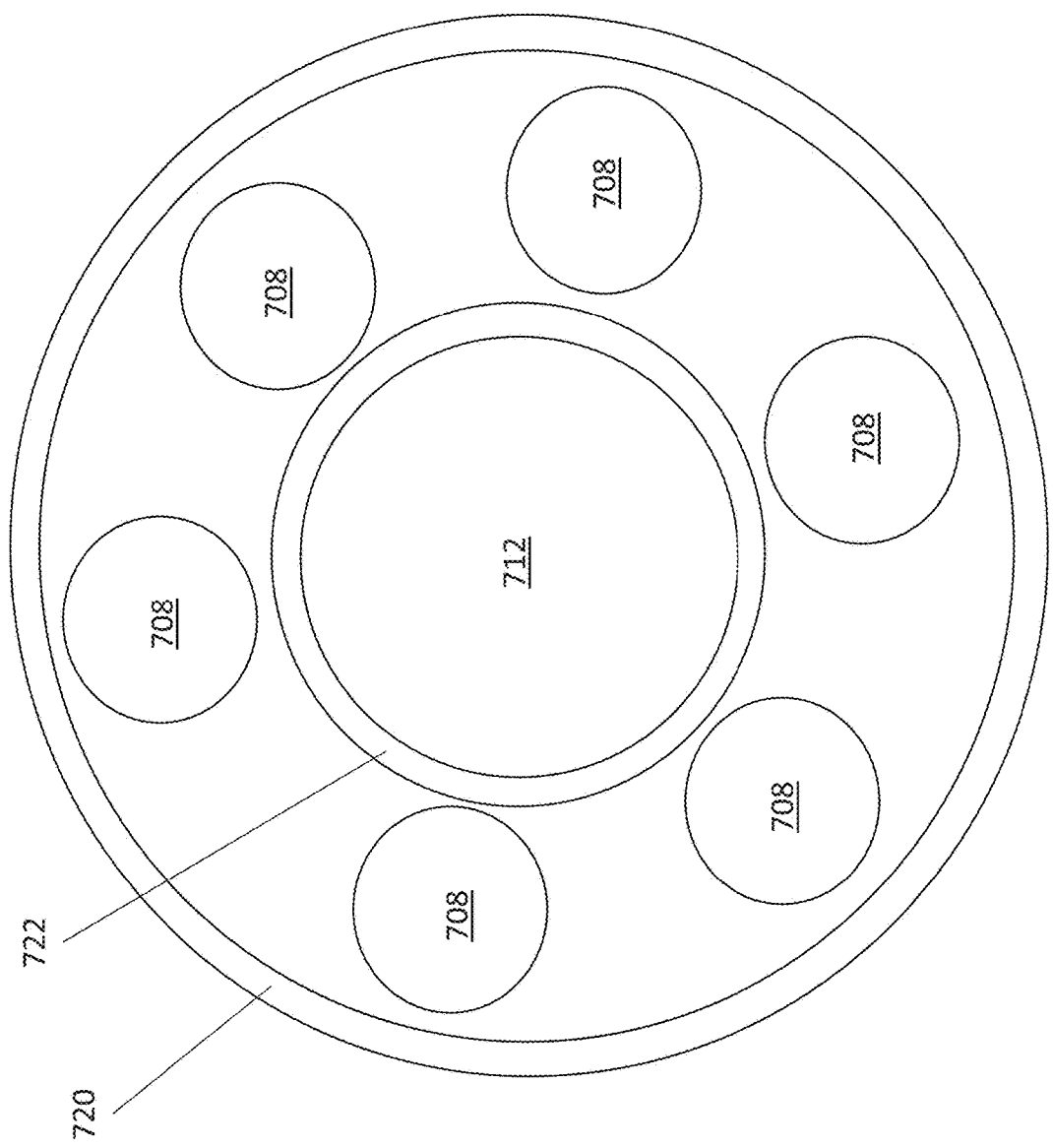
FIG. 8 is a cross section view of an infusion catheter at the junction between the infusion catheter, eluting arms, sealing member, and central axis member according to one embodiment.

Illustrated in FIG. 7 and FIG. 8, central axis member 712 passes through sealing member 722 to exit the lumen of shaft 720. Sealing member 722 is a lumen within shaft 720 having a distal end that is attached to the distal end of shaft 720. The inner diameter of the lumen of sealing member 722 and the outer diameter of central axis member 712 are dimensioned such that central axis member 712 slip fits within the sealing member lumen with a close clearance, enabling central axis member 712 to slide within the lumen of sealing member 722 while substantially preventing fluid from leaking out of the lumen of shaft 720. Described in another way, the close fit of central axis member 712 within the lumen of sealing member 722 enables leak-free movement of central axis member 712, even when infusion catheter 700 is delivering a fluid, between a high pressure in the lumen of shaft 720 and a low pressure outside of infusion catheter 700. In some embodiments, a small gap space can be present between the inner diameter of the lumen of sealing member 722 and the outer diameter of central axis member 712; a small amount of fluid may be permitted to enter the space, wherein the small amount of fluid effectively plugs the small gap space and prevents additional fluid from leaking out of the lumen of shaft 720, including pressurized fluid. Typically, drug delivery fluid comprises a viscosity that cannot easily flow through the close clearance or the small gap space. The ability of sealing member 722 to withstand leaking pressurized fluid within the lumen of shaft 720 can also be controlled by the length of sealing member 722. For example, a sealing member 722 having a longer length is able to withstand higher fluid pressures within the lumen of shaft 720 without leaking. Typical lengths of sealing member 722 can be between 1 and 10 mm, or as long as the length of a eluting arm 708.

Figure 9:
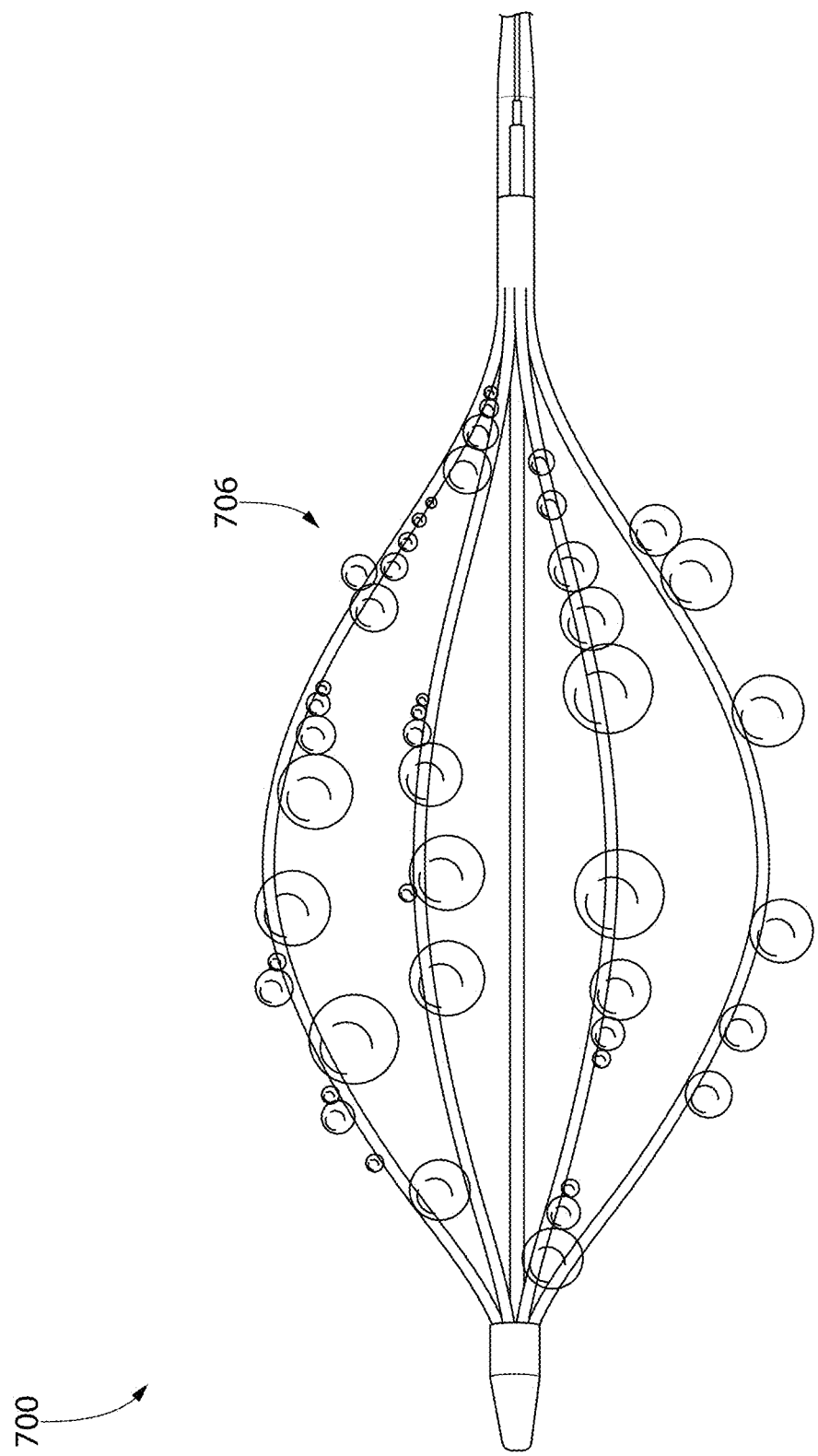
FIG. 9 is a side view of an infusion catheter eluting therapeutic through the eluting arms according to one embodiment.

The multiple eluting arms 708 deliver therapeutic fluid from shaft 720. In some embodiments, each eluting arm 708 has multiple infusion ports 710 fluidly connected to the lumen of each eluting arm 708. For example, the multiple infusion ports 710 can be laser drilled holes having diameters between 0.001 and 0.01 inches, with as many as 108 ports or more per eluting arm 708. In other embodiments, each eluting arm 708 has a porous surface or is spun from a fiber material, such that pressurized fluid within the lumen of each eluting arm 708 permeates through each eluting arm 708 (e.g., FIG. 9). Pressure-driven fluid delivered by permeating through eluting arms 708 feature more controlled and more consistent fluid release profiles. In some embodiments, the output flow rate of fluid from the multiple eluting arms 708 is matched with the input flow rate requirements of the intravenous (IV) pump settings for typical clinical drug delivery procedures, creating optimal back pressure within the multiple eluting arms 708 to release the fluid.

Figure 10A:
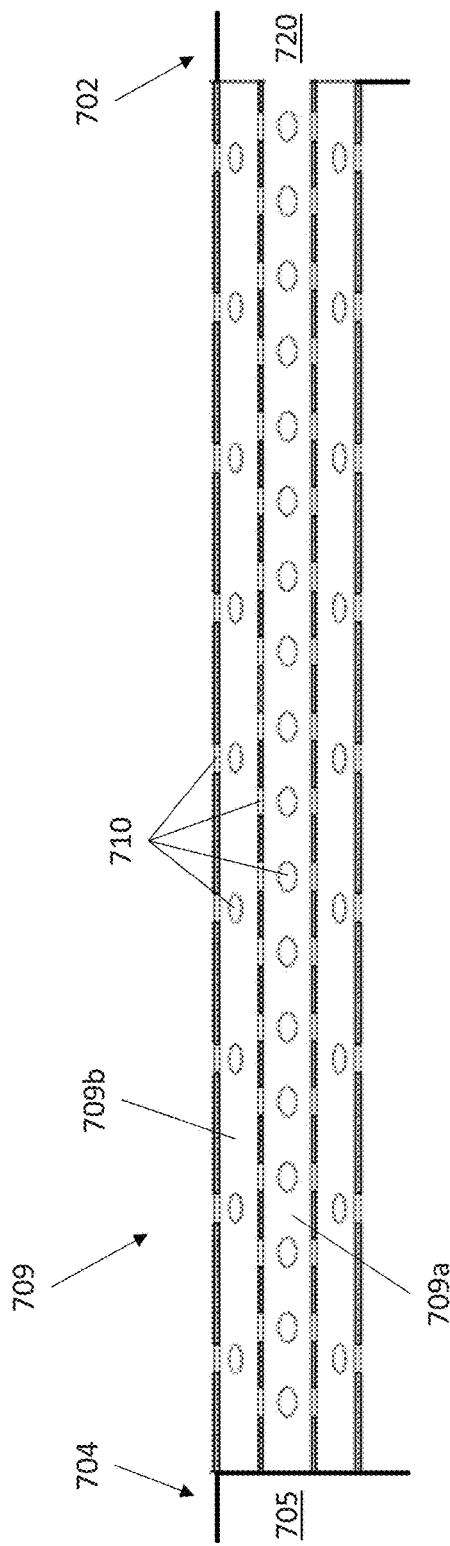
FIG. 10A and FIG. 10B is a side cross section view and a perspective cross section view, respectively, of an infusion catheter eluting arm having a double tube design according to one embodiment.
Figure 10B:
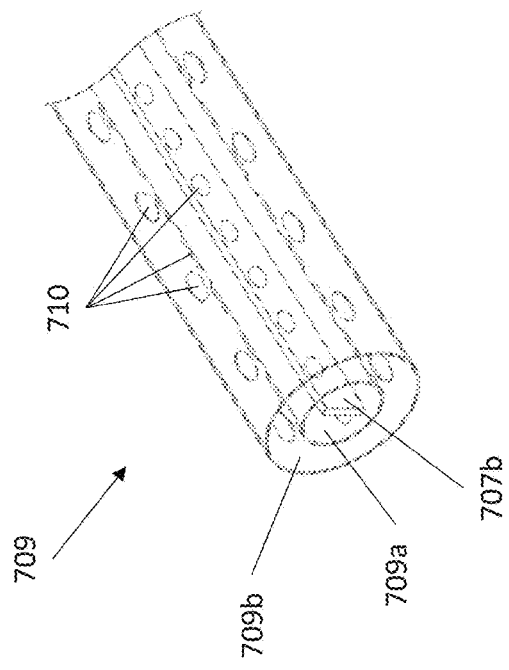

In some embodiments, the multiple eluting arms 708 have a double tube design. Referring now to FIG. 10A, an exemplary double tube eluting arm 709 is depicted. Double tube eluting arm 709 comprises an inner tube 709a positioned within the lumen of an outer tube 709b. Inner tube 709a comprises a lumen that is fluidly connected to shaft 720 at a proximal end 702 and is closed at a distal end 704 adjacent to distal end cap 705. Outer tube 709b is closed at both proximal end 702 and distal end 704. Inner tube 709a and outer tube 709b each comprise multiple infusion ports 710 that can be laser drilled holes having diameters between 0.001 and 0.01 inches. The multiple infusion ports 710 of inner tube 709a and outer tube 709b are fluidly connected to the lumen of their respective tube, such that a fluid delivered through shaft 720 is flowable into the lumen of inner tube 709a, through the multiple infusion ports 710 of inner tube 709a into the lumen of outer tube 709b, and through the multiple infusion ports 710 of outer tube 709b to exit double tube eluting arm 709. In one embodiment, inner tube 709a comprises a first porosity and outer tube 709b comprises a second porosity, wherein the first porosity is greater than the second porosity. Inner tube 709a thereby has a greater flow rate across its infusion ports 710 than the flow rate of outer tube 709b across its infusion ports 710. The difference in porosity can be achieved by the number of infusion ports 710, the size of each infusion ports 710, or a combination thereof. Fluid delivered through shaft 720 therefore quickly exits inner tube 709a to fill the lumen of outer tube 709b before exiting outer tube 709b at a slower, more uniform rate. FIG. 10B depicts a cross section of a double tube eluting arm 709 supported by a tine 707b inserted into inner tube 709a, as described elsewhere herein.

The multiple eluting arms 708 and double tube eluting arms 709 can be constructed from any suitable material, including but not limited to polytetrafluoroethylene (PTFE), expanded PTFE (ePTFE), Tyvek, and Kynar polyvinylidene fluoride (PVDF).

Figure 11A:
FIG. 11A is a side view of a nitinol frame according to one embodiment.
Figure 11B:
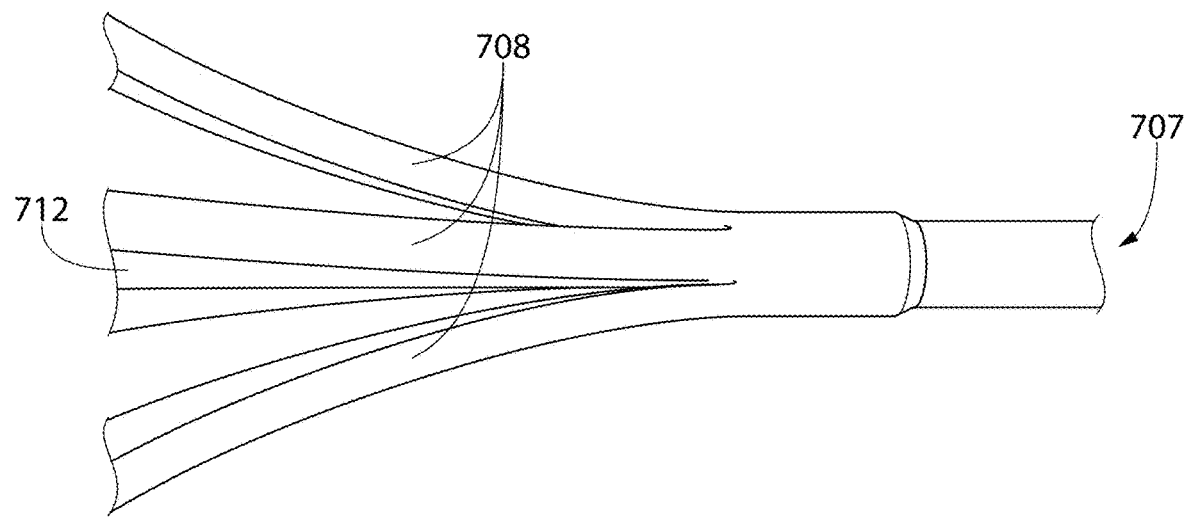
FIG. 11B is a side view of eluting arms fitted to a frame according to one embodiment.
Figure 12:
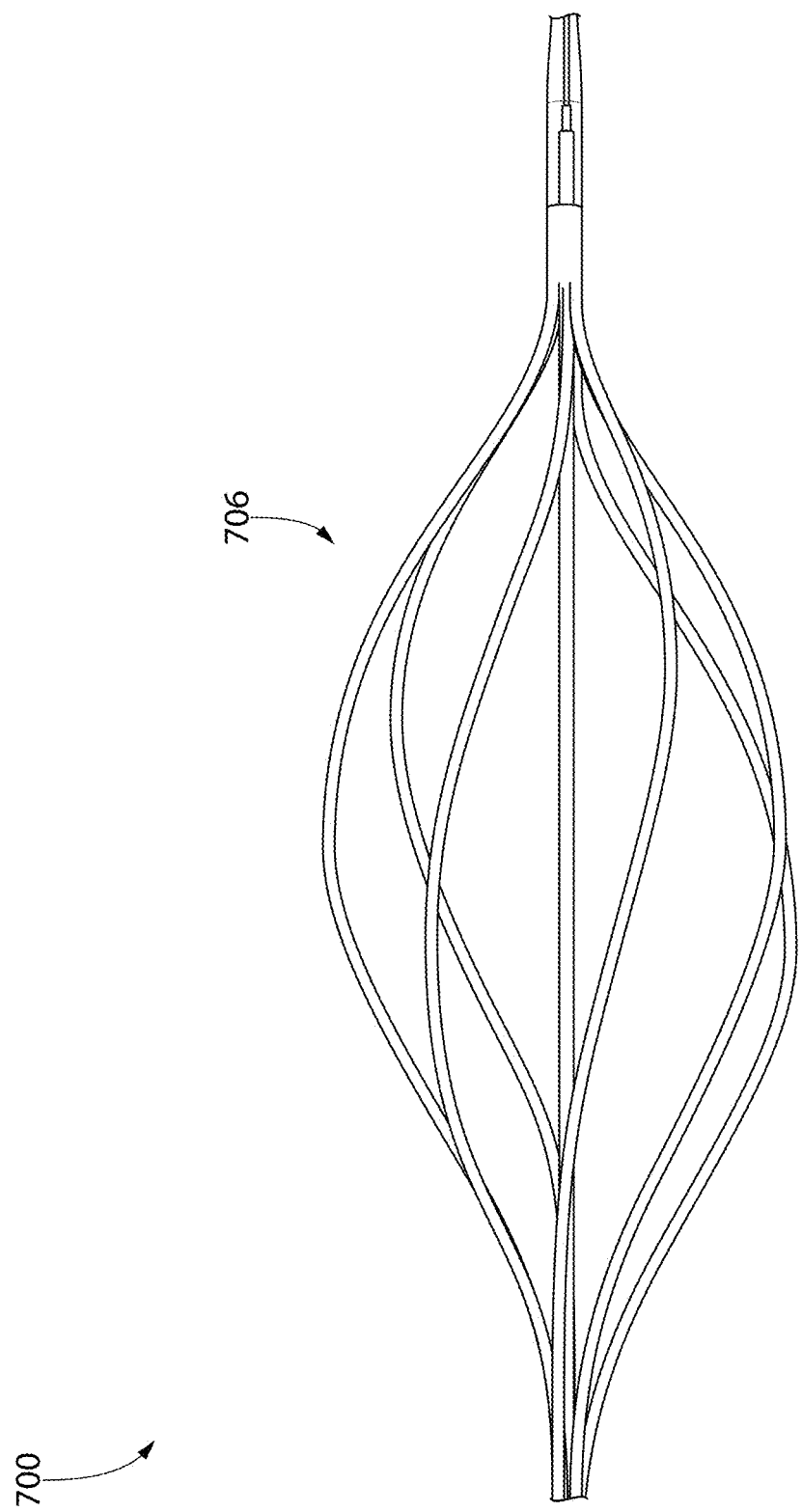
FIG. 12 is a side view of an infusion catheter with eluting arms fitted to a frame set to a spiral shape according to one embodiment.
Figure 13:
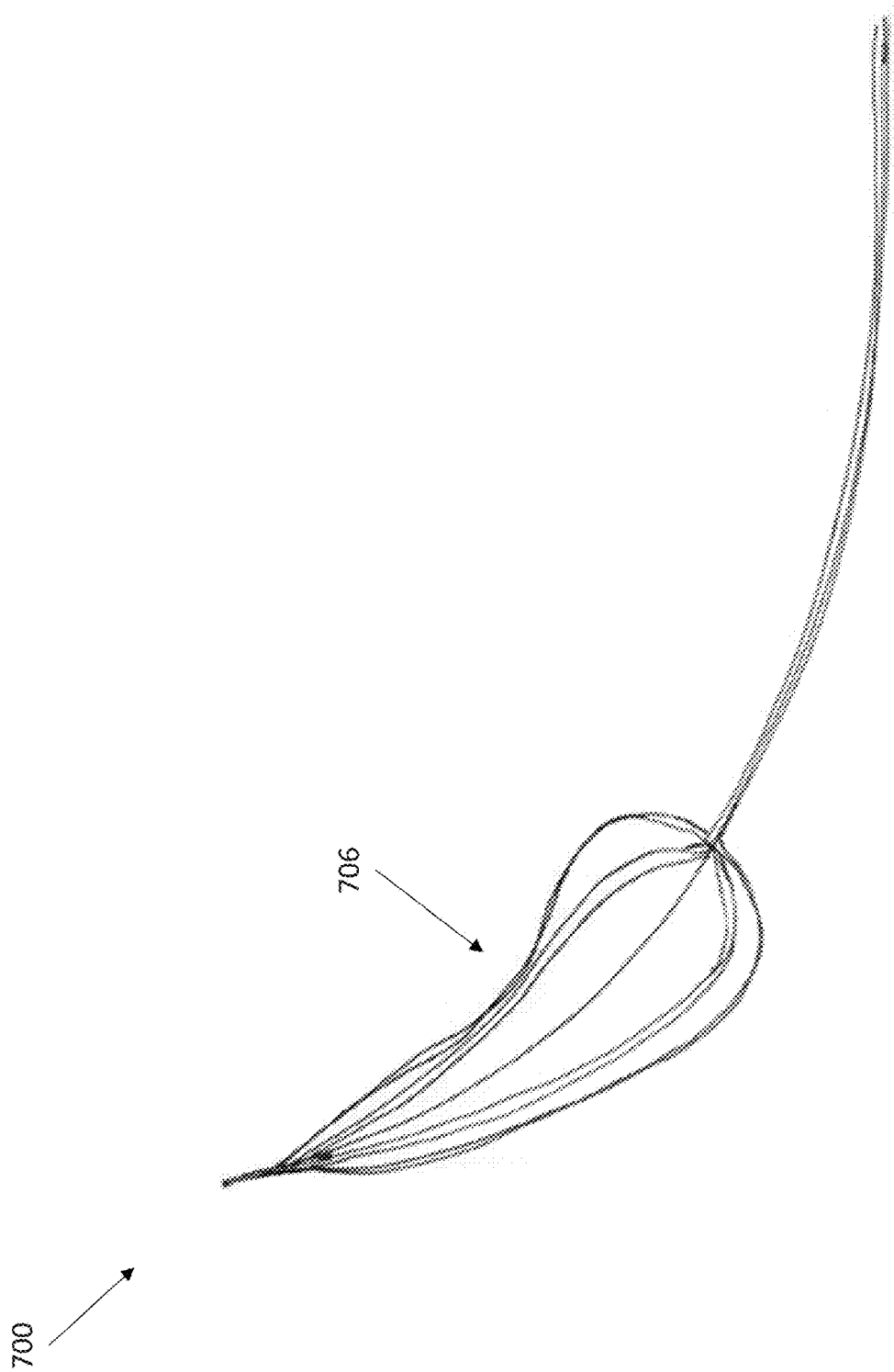
FIG. 13 is a side view of an infusion catheter with eluting arms fitted to a frame set to a pear shape according to one embodiment.

Illustrated in FIG. 11A and FIG. 11B, the multiple eluting arms 708 can be supported by frame 707. Frame 707 has a proximal ring 707a connecting multiple tines 707b, wherein each tine 707b can be attached to the exterior of the multiple eluting arms 708 or fit within the lumens of the multiple eluting arms 708 or inner tube 709a of double tube eluting arms 709. In some embodiments, frame 707 is constructed from a shape memory polymer or a shape memory metal such as nitinol. The strength and stiffness of the multiple tines 707b can be varied by controlling the width and thickness of the multiple tines 707b. The multiple tines 707b can be any suitable shape, such as straight (FIG. 11A) or spiraled (FIG. 12). In some embodiments, frame 707 can have a predetermined shape, such as a shape adapted for a specific vessel or for a specific procedure. The predetermined shape is revealed when the infusion catheter 700 is configured from a relaxed state to a stressed or deployed state by sliding central axis member 712. For example, in FIG. 13, frame 707 has a predetermined pear shape that may provide superior performance in pulmonary artery procedures, wherein after deploying infusion catheter 700, the predetermined shape of frame 707 expands the multiple eluting arms 708 outwards at the proximal end of eluting portion 706 and tapers the multiple eluting arms 708 inwards at the distal end of eluting portion 706.

Advantageously, frame 707 of infusion catheter 700 also allows for mechanical movement of the catheter to exert pressure on the clot for creating a large channel in the middle of the clot to enhance blood flow through the clot (as described above) or to mechanically break apart a clot. By repeatedly switching the infusion catheter 700 between a relaxed state and a stressed or deployed state, the movement of the multiple eluting arms 708 or double tube eluting arms 709 macerates the clot while delivering clot busting therapeutic fluid upon contact at the same time. The multiple eluting arms 708 or double tube eluting arms 709 are also able to trap and capture clots upon deployment.

Figure 14:
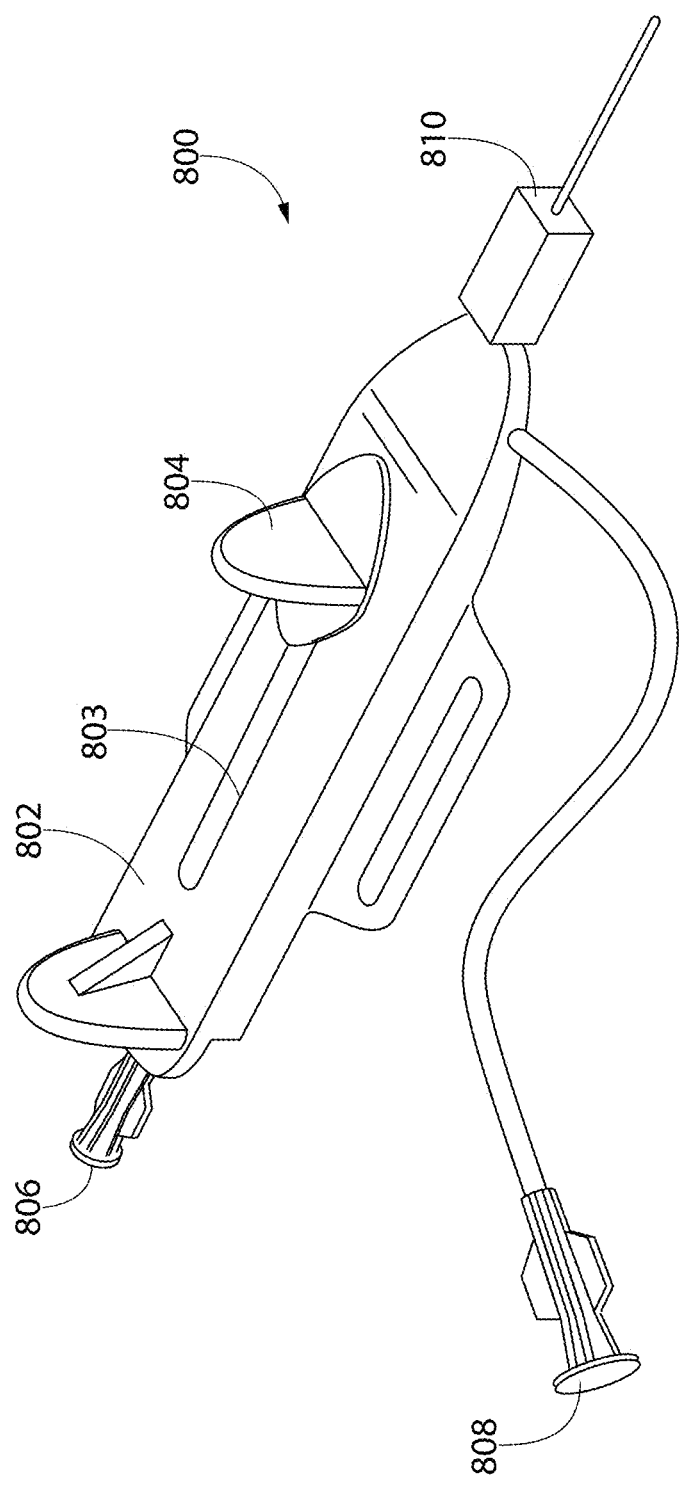
FIG. 14 is a perspective view of an infusion catheter handle unit according to one embodiment.

Referring now to FIG. 14, an exemplary handle 800 is depicted. Handle 800 connects to the proximal end of any of the catheters of the present invention to provide an operator with a grip as well as ports for the insertion/removal of components such as guide wires and therapeutic fluid. In some embodiments, handle 800 comprises housing 802, slider 804, first port 806, second port 808, and third port 810. Housing 802 is a casing holding the components of handle 800 and includes track 803. Slider 804 slides along track 803 and is linked to central axis member 712 (FIG. 7), such that slider 804 can be slid to a proximal position to retract central axis member 712, and slid to a distal position to relax central axis member 712. In this fashion, slider 804 is able to control the deployment of eluting portion 706 and to switch the infusion catheter 700 between a relaxed state and a stressed or deployed state. In certain embodiments, housing 802 further comprises a locking member. The locking member can be any suitable mechanism capable of arresting the movement of slider 804, such as a switch, a tab, a detent, and the like. First port 806 is connected to a lumen fluidly connectable to a guidewire lumen of central axis member 712, such that a guidewire can be inserted or removed from central axis member 712 by way of first port 806. Second port 808 is connected to a lumen fluidly connectable to the lumen of shaft 720, such that therapeutic fluid may be inserted or removed from the lumen of shaft 720 by way of second port 808. Third port 810 is the point of connection between the lumen of first port 806, the lumen of second port 808, and the proximal end of infusion catheter 700. While not pictured in FIG. 14, the lumen of first port 806 and the lumen of second port 808 join together at a Y-connector interface within housing 802, such that the lumen of first port 806 enters the lumen of second port 808 to run in parallel in a manner that mirrors central axis member 712 running within shaft 720. In certain embodiments, at the Y-connector interface, a second sealing member 722 is provided, through which the lumen of first port 806 is able to enter the lumen of second port 808 without fluid leakage.

A method for treating thrombus in a vessel includes the steps of advancing a catheter at least partially through a thrombus within a vessel, expanding at least a portion of the catheter within the thrombus and away from a longitudinal axis of the catheter, simultaneously infusing a therapeutic agent through a first plurality of openings aimed towards the longitudinal axis and a second plurality of openings of the aimed away from the longitudinal axis while the catheter is expanded. In one embodiment, the step of expanding comprises shifting the catheter from a stressed state to a relaxed state. In one embodiment, the step of expanding includes retracing a sheath coaxially loaded over the catheter. In one embodiment, the step of expanding comprises sliding a central wire connected to a first end of the expended portion of the catheter relative to a second end of the expanded portion that is coaxially loaded and slidable over the central wire. In one embodiment, the catheter is expanded to a spiral shape. In one embodiment, the catheter is expanded to a conical spiral shape. In one embodiment, the catheter is expanded to a pear shape. In one embodiment, the catheter comprises a plurality of branches that diverge away from the longitudinal axis from a first point along the longitudinal axis and converge towards the longitudinal axis to a second point along the longitudinal axis, wherein the second point is distal of the first point. In one embodiment, the plurality of branches are positioned radially around the entire longitudinal axis when the catheter is expanded. In one embodiment, the plurality of branches are positioned radially around less than 270 degrees of the longitudinal axis when the catheter is expanded. In one embodiment, the plurality of branches are positioned radially around 180 degrees or less of the longitudinal axis when the catheter is expanded. The catheter can be inserted into any vessel afflicted by a thrombosis or an embolism, including but not limited to the inferior vena cava, the superior vena cava, the iliac veins, the aorta, the pulmonary artery, and the pulmonary vein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out exemplary embodiments of the present invention, and are not to be construed as limiting in any way the remainder of the disclosure.

Example 1: Treatment of Acute Large Vessel Venous Thromboembolism

The goal of the present study is to develop preclinical evidence for the safety and efficacy of the novel interventional catheter (NIC) in the treatment of acute large vessel venous thromboembolism. The NIC has a unique design that utilizes both mechanical and pharmacological features to improve thrombolytic efficacy. It accomplishes this by harnessing a patient's own clot dissolving mechanisms (endogenous fibrinolysis) with small doses of exogenous thrombolytic agent. The design includes multiple expandable parallel infusion channels that exert a gentle sustained pressure on the blood clot and creates a large passageway through the blood clot that markedly enhances blood flow. This prompt restoration of flow through an occluded large vein, such as a pulmonary artery, can be crucial in stabilizing a crashing patient with a pulmonary embolism. In addition, the nitinol reinforced infusion limbs, when expanded, lead to thrombolysis at different cross sectional locations in a large vessel. Another feature of this device that enhances thrombolysis is the ease of expanding and collapsing the infusion basket, which exposes a much larger surface area of the thrombus to thrombolytic action of both the endogenous as well as the exogenous thrombolytic agents.

Animal Model: A new porcine model based on the Yorkshire pig has been developed for large vessel venous thromboembolism. An 8F sheath is placed into the femoral vein and an inferior vena cavogram is performed. An IVC filter (Denali Bard filter) is deployed in the infra-renal IVC and correct placement is documented by a repeat venogram. The sheath is then upsized to 14F and advanced into the IVC just above the bifurcation. The sheath dilator and the wires are removed. The 12F sheath containing the clot is then advanced into the 14F sheath and the clot is injected into the IVC by pushing 20 mL of saline into the side arm of the 12F sheath under pressure. Once the clot is injected into the cava it gets trapped by the filter and produces a complete occlusion of the IVC, which is documented by a repeat cavogram. If there is persistent flow, another clot is injected from a different sheath. This process is repeated if necessary until the IVC is completely occluded.

In Vitro Clot Preparation: Blood samples (50 cc) are obtained from a test animal (pig) and placed in 12F sheaths (45 cm long) and allowed to clot at room temperature for 12 hours. The sheaths are then stored in a refrigerator at 4° C. for 7-10 days. Since the sheaths contain no anticoagulants, a fully retracted clot is formed. This blood clot is injected into the animal by connecting a 20 cc syringe to the sidearm of the sheath and pushing 20 cc of normal saline into the sheath. The extracted blood clot gets pushed into the inferior vena cava of the animal.

Preparation of Reconstituted Tissue Plasma Activator: The reconstituted tissue plasma activator (tPA) solution is made by reconstituting 50 mg of tPA with 100 cc of sterile water. 40 cc of this reconstituted medication is injected into a 1000 mL bag of half normal saline (final concentration of 0.02 mg of tPA/mL). The reconstituted tPA is infused at 200 mL/hour via the novel infusion catheter. This will infuse 20 mg over 5 hours.

Pharmacomechanical Thrombolysis: A glide wire is used to cross the occluded IVC and positioned in the supra-renal IVC. This wire is then exchanged for a 0.18 wire using a 4F support catheter. This wire is positioned within the thrombus and used to advance the NIC. The NIC infusion basket is then expanded by retracting the NIC inner shaft. Following this, a cavogram is repeated to assess the impact of this mechanical action on the blood flow through the clot. A power spray of 2 mg of tPA diluted in 10 mL of normal saline is performed followed by a tPA infusion at 200 mL/hour via the sidearm of the device. Venograms are performed every hour to assess clot lysis and restoration of flow across the occluded IVC. During this time, heparin is infused via the sidearm of the sheath at 12 U/kg (rate of 500 U/hour). Clot lysis is assessed using angiographic cine runs and the protocol used for the national venous registry study. Safety of the NIC is evaluated by monitoring the pigs for bleeding rates for 7 days. During these 7 days, the pigs are treated with lovenox injections at 1 mg/kg twice daily.

Figure 15:
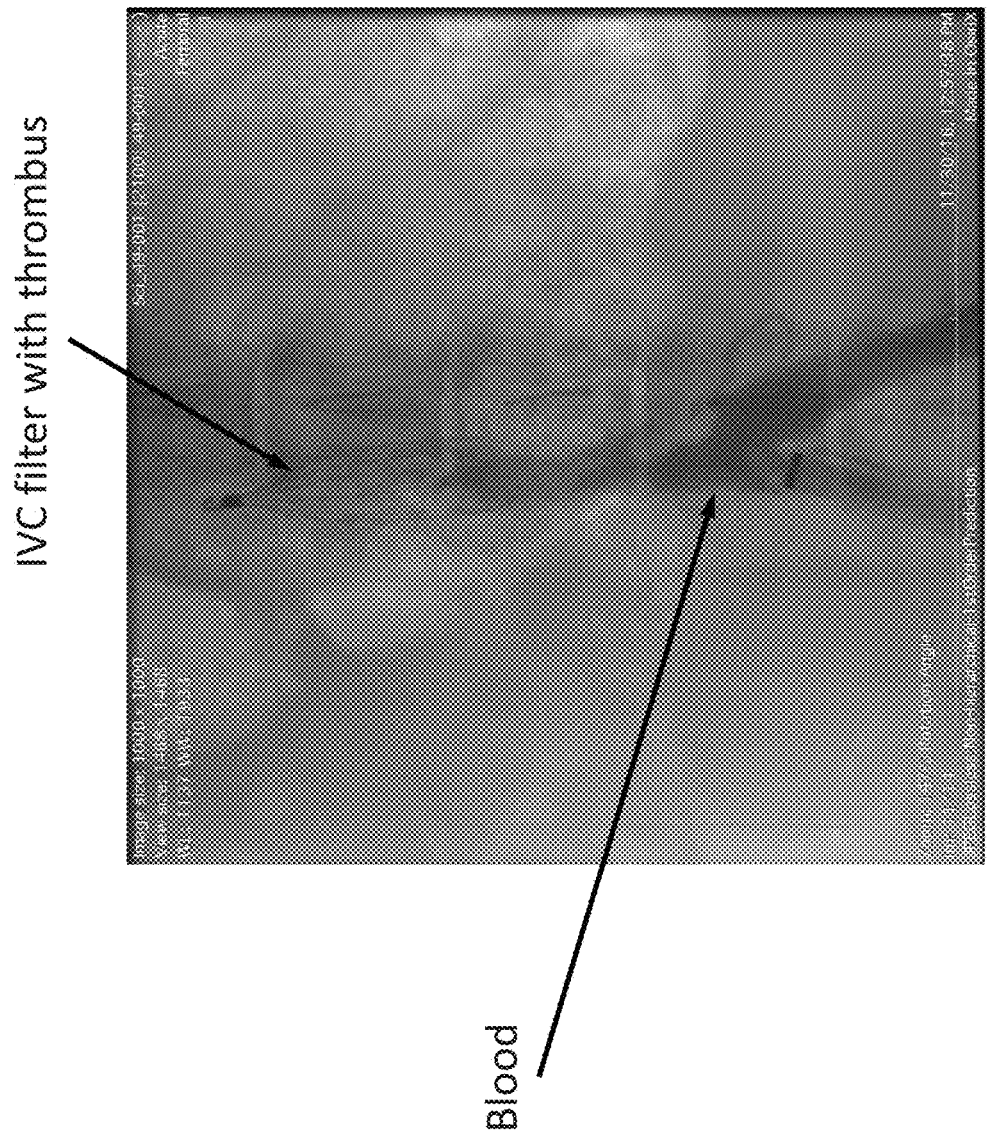
FIG. 15 is an image of a porcine inferior vena cava (IVC) model showing blocked blood flow in the IVC due to the insertion of a thrombus into an IVC filter.
Figures 16A, 16B:
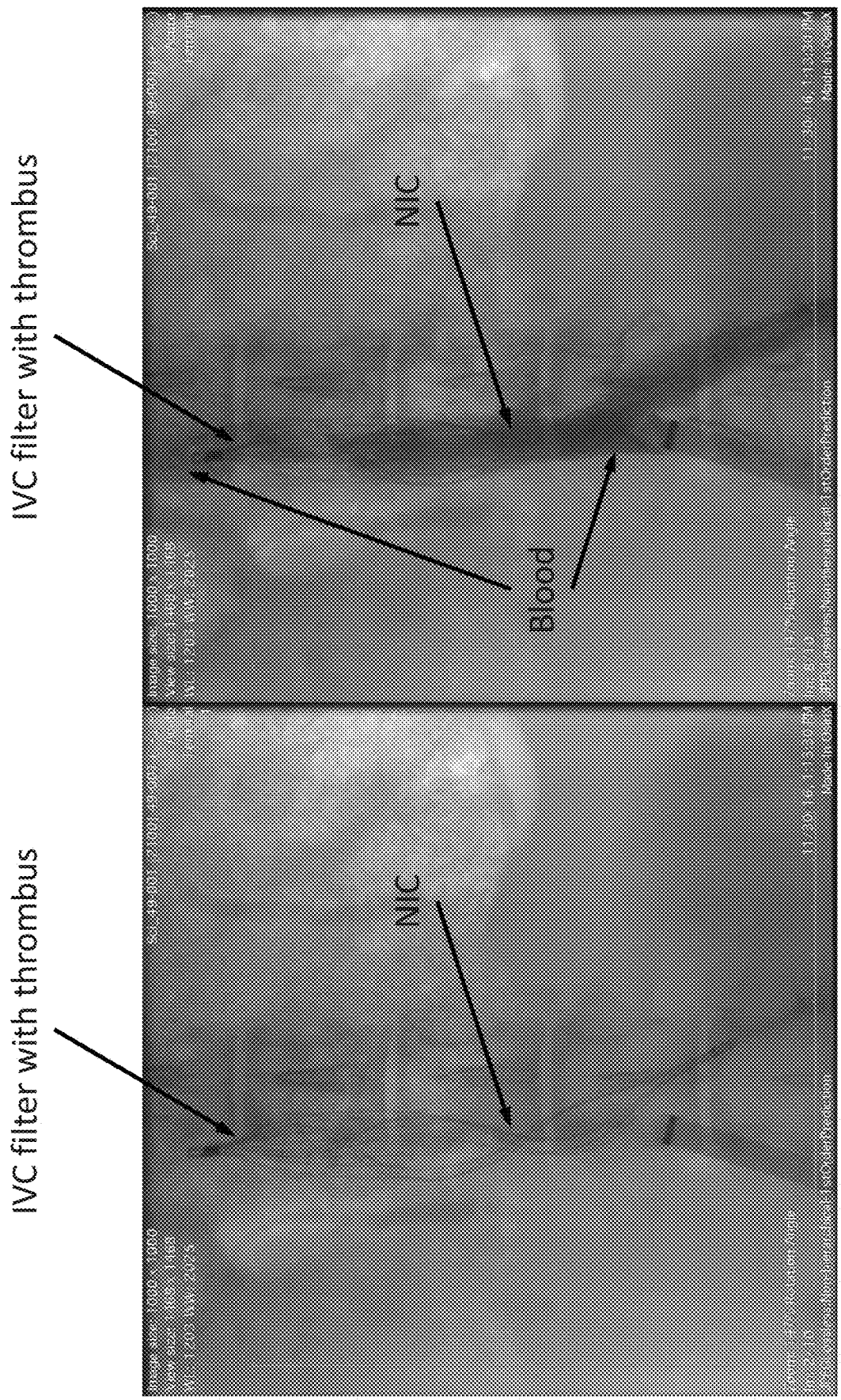
FIG. 16A and FIG. 16B are images of a porcine IVC model after insertion of an infusion catheter according to one embodiment (FIG. 16A) and the restoration of an amount of blood flow (FIG. 16B).
Figures 17A, 17B, 17C:
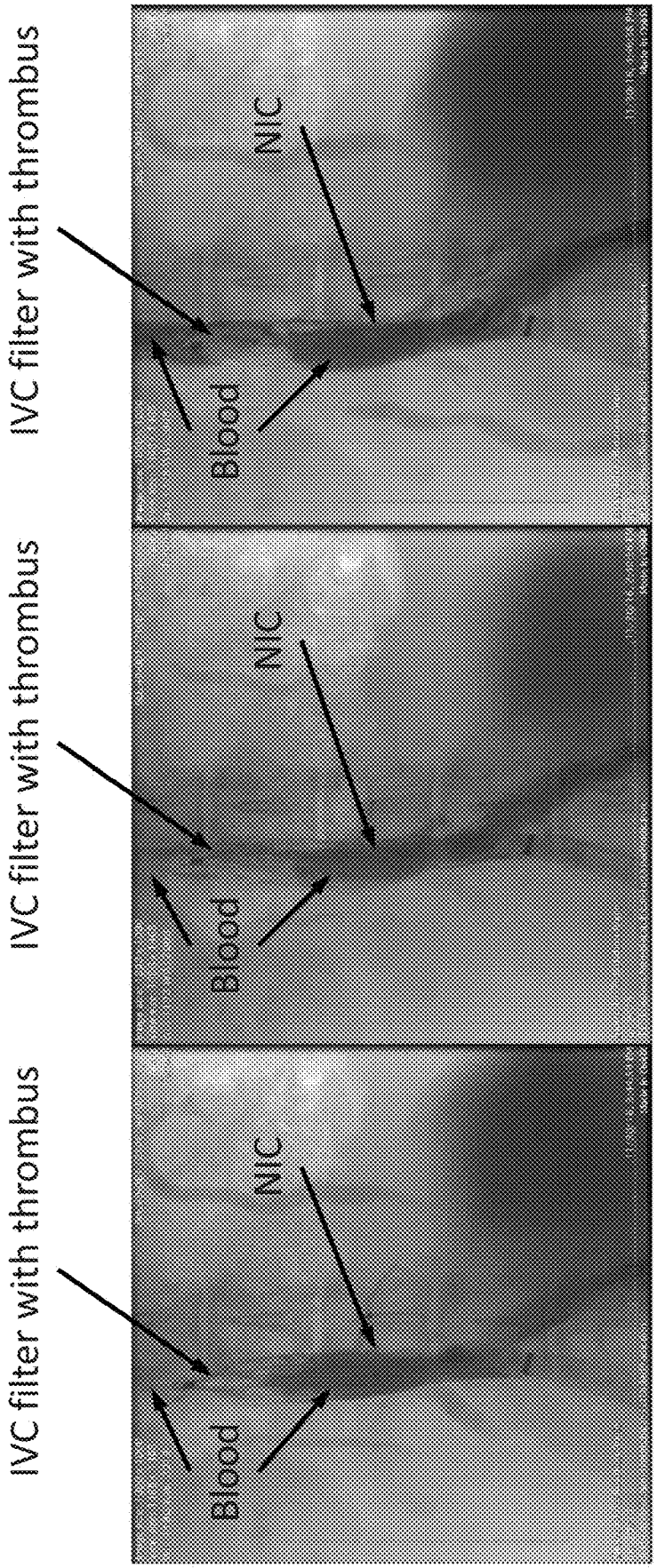
FIG. 17A through FIG. 17C are images of a porcine IVC model at one hour (FIG. 17A), two hours (FIG. 17B), and three hours (FIG. 17C) post-insertion of an infusion catheter according to one embodiment.
Figures 18A, 18B:
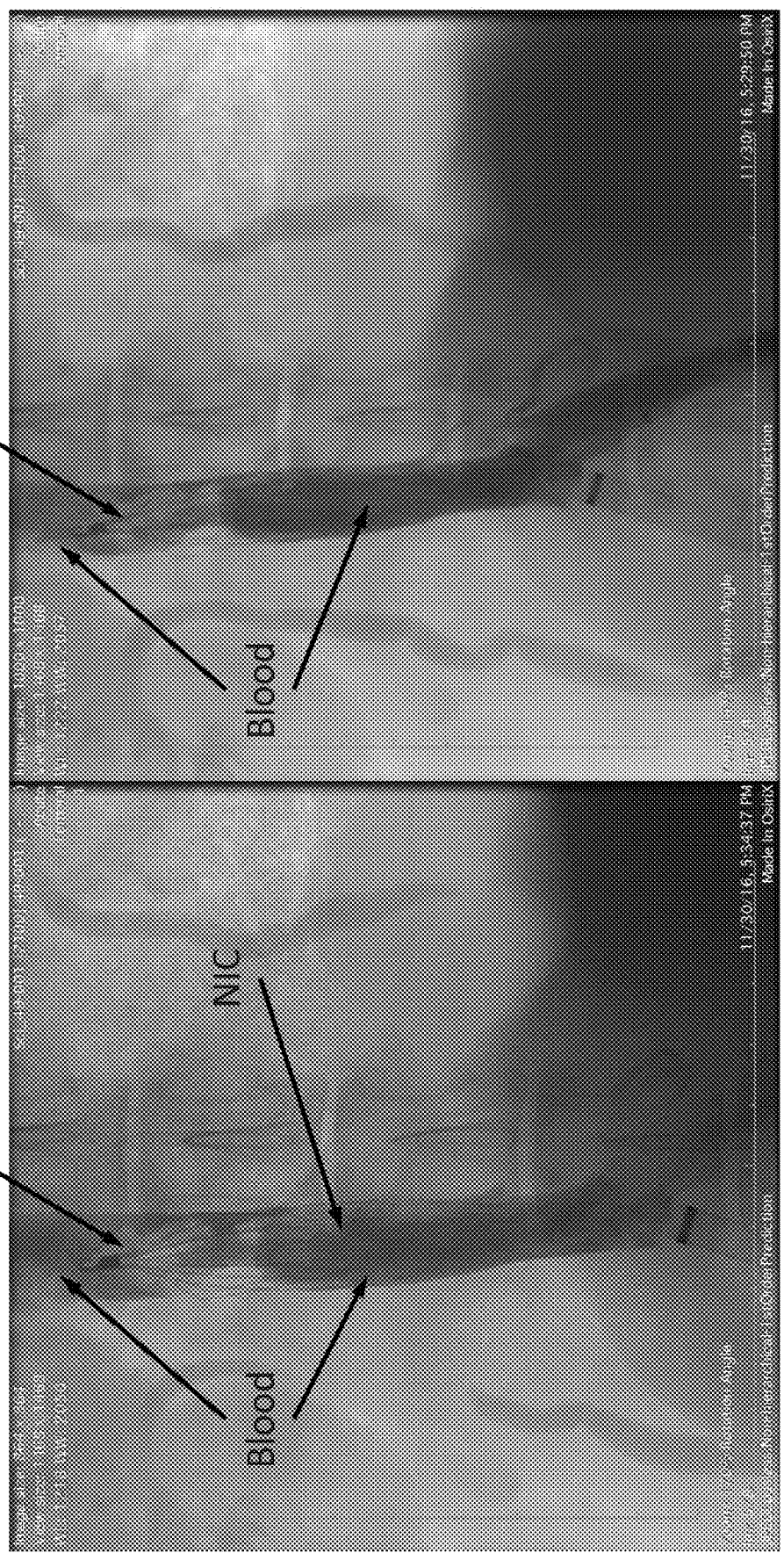
FIG. 18A and FIG. 18B are images of a porcine IVC model at four hours post-insertion of an infusion catheter according to one embodiment (FIG. 18A) and the continued blood flow after the catheter has been removed (FIG. 18B).

Example 2: Catheter for the Treatment of Acute Pulmonary Embolism and Large Vessel Deep Vein Thrombosis A porcine model of inferior vena cava (IVC) was created by placing an IVC filter in a pig IVC, then injecting a large volume of thrombus into the IVC, which was trapped in the IVC filter and produced an IVC occlusion with complete cessation of blood flow (FIG. 15). FIG. 16A shows the insertion of the novel interventional catheter (NIC) into the thrombus, wherein FIG. 16B shows the mechanical effect of deploying the NIC creates a channel in the thrombus and allows blood flow through the thrombus to markedly enhance clot dissolution by bringing endogenous fibrinolytic agents into the thrombus. FIG. 17A through FIG. 17C shows steady improvement in blood flow after 1 hour (FIG. 17A), 2 hours (FIG. 17B), and 3 hours (FIG. 17C) post-insertion of the NIC. FIG. 18A shows markedly improved flow at 4 hours, which typically is not seen with conventional catheter-directed thrombolysis even at 24 hours. In FIG. 18B, the NIC is removed with continued blood flow.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention.

What is claimed is:

1. An infusion catheter comprising:
   an elongate flexible shaft comprising a wall and a lumen extending a length between a proximal end and a distal end;
   a sealing member within the shaft lumen comprising a wall and a lumen extending a length between a proximal end and a distal end, the distal end of the sealing member being attached to the distal end of the shaft;
   a slidable, retractable elongate central axis member extending through the shaft and sealing member lumens; and
   an eluting member having a lumen fluidly connected to the distal end of the shaft lumen, wherein the eluting member and the elongate central axis member connect to a distal end cap.

2. The infusion catheter of claim 1 further comprising:
   a plurality of eluting members, each eluting member having a lumen fluidly connected to the distal end of the shaft lumen.

3. The infusion catheter of claim 2, wherein the plurality of eluting members extend radially around the central axis member.

4. The infusion catheter of claim 1, further comprising a frame having at least one tine within the lumen of the eluting member.

5. The infusion catheter of claim 4, wherein the frame is constructed from a shape memory material.

6. The infusion catheter of claim 5, wherein the shape memory material is nitinol.

7. The infusion catheter of claim 5, wherein the shape memory material forms a pear shape.

8. The infusion catheter of claim 1, wherein the eluting member comprises at least one infusion port fluidly connected to the eluting member lumen.

9. The infusion catheter of claim 8, wherein the infusion port is a laser drilled hole having a diameter between 0.001 to 0.01 inches.

10. The infusion catheter of claim 1, wherein the eluting member comprises a porous surface.

11. The infusion catheter of claim 10, wherein the porous surface elutes pressurized fluid from the eluting member lumen.

12. The infusion catheter of claim 11, wherein the porous surface is constructed from a material selected from the group consisting of:
   polytetrafluoroethylene (PTFE), expanded PTFE (ePTFE), Tyvek, and Kynar polyvinylidene fluoride (PVDF).

13. The infusion catheter of claim 1, wherein the eluting member is positioned within an outer tube having a surface comprising at least one infusion port fluidly connected to a lumen, a closed proximal end, and a closed distal end.

14. The infusion catheter of claim 13, wherein the surface of the outer tube is less porous than the eluting member.

15. The infusion catheter of claim 1, wherein the inner diameter of the sealing member lumen and the outer diameter of the central axis member are dimensioned such that central axis member slip fits within the sealing member lumen with a close clearance permitting movement of the central axis member while preventing fluid leakage through the close clearance.

16. The infusion catheter of claim 15, wherein the central axis member is slidable through the sealing member lumen and the shaft lumen, the shaft lumen having a fluid pressure higher than a fluid pressure outside of the shaft lumen, without leaking fluid through the close clearance.

17. The infusion catheter of claim 1, wherein the distance between a distal end cap and the distal end of the shaft is reversibly shortened by sliding central axis member through the sealing member lumen, thereby expanding the eluting member away from the central axis member.

18. The infusion catheter of claim 1, wherein the central axis member comprises a guidewire lumen.

19. An infusion system kit comprising:
the infusion catheter of claim 1; and
a guidewire configured for insertion through a guidewire lumen of the central axis member.

20. An infusion catheter comprising:
an elongate flexible shaft comprising a wall and a lumen extending a length between a proximal end and a distal end;
a sealing member within the shaft lumen comprising a wall and a lumen extending a length between a proximal end and a distal end, the distal end of the sealing member being attached to the distal end of the shaft;
a slidable, retractable elongate central axis member extending through the shaft and sealing member lumens; and
a plurality of eluting members, each eluting member having a lumen fluidly connected to the distal end of the shaft lumen.

21. An infusion catheter comprising:
an elongate flexible shaft comprising a wall and a lumen extending a length between a proximal end and a distal end;
a sealing member within the shaft lumen comprising a wall and a lumen extending a length between a proximal end and a distal end, the distal end of the sealing member being attached to the distal end of the shaft;
a slidable, retractable elongate central axis member extending through the shaft and sealing member lumens;
an eluting member having a lumen fluidly connected to the distal end of the shaft lumen; and
a frame having at least one tine within the lumen of the eluting member.

22. An infusion catheter comprising:
an elongate flexible shaft comprising a wall and a lumen extending a length between a proximal end and a distal end;
a sealing member within the shaft lumen comprising a wall and a lumen extending a length between a proximal end and a distal end, the distal end of the sealing member being attached to the distal end of the shaft;
a slidable, retractable elongate central axis member extending through the shaft and sealing member lumens; and
an eluting member having a lumen fluidly connected to the distal end of the shaft lumen, wherein the eluting member is positioned within an outer tube having a surface comprising at least one infusion port fluidly connected to a lumen, a closed proximal end, and a closed distal end.

23. An infusion catheter comprising:
an elongate flexible shaft comprising a wall and a lumen extending a length between a proximal end and a distal end;
a sealing member within the shaft lumen comprising a wall and a lumen extending a length between a proximal end and a distal end, the distal end of the sealing member being attached to the distal end of the shaft;
a slidable, retractable elongate central axis member extending through the shaft and sealing member lumens, wherein the central axis member comprises a guidewire lumen; and
an eluting member having a lumen fluidly connected to the distal end of the shaft lumen.

24. An infusion catheter comprising:
an elongate flexible shaft comprising a wall and a lumen extending a length between a proximal end and a distal end;
a sealing member within the shaft lumen comprising a wall and a lumen extending a length between a proximal end and a distal end, the distal end of the sealing member being attached to the distal end of the shaft;
a slidable, retractable elongate central axis member extending through the shaft and sealing member lumens; and
an eluting member having a lumen fluidly connected to the distal end of the shaft lumen.

25. An infusion system kit comprising:
an infusion catheter comprising:
an elongate flexible shaft comprising a wall and a lumen extending a length between a proximal end and a distal end,
a sealing member within the shaft lumen comprising a wall and a lumen extending a length between a proximal end and a distal end, the distal end of the sealing member being attached to the distal end of the shaft,
a slidable, retractable elongate central axis member extending through the shaft and sealing member lumens, and
an eluting member having a lumen fluidly connected to the distal end of the shaft lumen; and
a guidewire configured for insertion through a guidewire lumen of the central axis member.

* * * * *